United States Patent
Minamide et al.

(10) Patent No.: US 12,137,978 B2
(45) Date of Patent: Nov. 12, 2024

(54) BLOOD FLOW MEASUREMENT APPARATUS, METHOD OF CONTROLLING THE SAME, AND RECORDING MEDIUM

(71) Applicant: Topcon Corporation, Tokyo (JP)

(72) Inventors: Kana Minamide, Tokyo (JP); Masahiro Akiba, Wako (JP)

(73) Assignee: TOPCON CORPORATION, Tokyo (JP)

( * ) Notice: Subject to any disclaimer, the term of this patent is extended or adjusted under 35 U.S.C. 154(b) by 666 days.

(21) Appl. No.: 17/417,760

(22) PCT Filed: Dec. 25, 2019

(86) PCT No.: PCT/JP2019/050980
§ 371 (c)(1),
(2) Date: Jun. 24, 2021

(87) PCT Pub. No.: WO2020/138224
PCT Pub. Date: Jul. 2, 2020

(65) Prior Publication Data
US 2022/0007935 A1    Jan. 13, 2022

(30) Foreign Application Priority Data
Dec. 28, 2018    (JP) .................. 2018-246992

(51) Int. Cl.
*A61B 3/12*    (2006.01)
*A61B 3/10*    (2006.01)
*A61B 5/00*    (2006.01)

(52) U.S. Cl.
CPC ............ *A61B 3/1233* (2013.01); *A61B 3/102* (2013.01); *A61B 5/489* (2013.01); *A61B 5/4893* (2013.01)

(58) Field of Classification Search
CPC ....... A61B 3/1233; A61B 3/102; A61B 5/489; A61B 5/4893; A61B 3/12; G06T 2207/10101
See application file for complete search history.

(56) References Cited

U.S. PATENT DOCUMENTS

2008/0204655 A1    8/2008    Kikawa et al.
2011/0319775 A1    12/2011   Fujii et al.
(Continued)

FOREIGN PATENT DOCUMENTS

JP    2007-319403 A    12/2007
JP    2008-206684 A    9/2008
(Continued)

OTHER PUBLICATIONS

International Search Report and Written Opinion mailed on Mar. 17, 2020, received for PCT Application PCT/JP2019/050980, Filed on Dec. 25, 2019, 10 pages including English Translation.
(Continued)

Primary Examiner — Mustak Choudhury
Assistant Examiner — K Muhammad
(74) Attorney, Agent, or Firm — XSENSUS LLP

(57) ABSTRACT

A blood flow measurement apparatus of an aspect example includes a scanning optical system, a front image acquiring unit, a region-of-interest determining processor, a scan controller, and a blood flow information acquiring unit. The scanning optical system applies OCT scanning to a fundus of a subject's eye. The front image acquiring unit acquires a front image of the fundus. The region-of-interest determining processor determines a region of interest that intersects a blood vessel by analyzing the front image based on a condition set in advance. The scan controller controls the scanning optical system to apply a repetitive OCT scan to the region of interest. The blood flow information acquiring (Continued)

unit acquires blood flow information based on data collected by the repetitive OCT scan.

9 Claims, 11 Drawing Sheets

(56) References Cited

U.S. PATENT DOCUMENTS

| | | | |
|---|---|---|---|
| 2012/0218517 A1 | 8/2012 | Imamura | |
| 2013/0229622 A1 | 9/2013 | Murase et al. | |
| 2014/0063458 A1 | 3/2014 | Imamura | |
| 2014/0073917 A1 | 3/2014 | Huang et al. | |
| 2015/0313466 A1 | 11/2015 | Yoshida | |
| 2016/0157737 A1 | 6/2016 | Huang et al. | |
| 2016/0220112 A1 | 8/2016 | Schmoll | |
| 2016/0287068 A1 | 10/2016 | Murase et al. | |
| 2016/0302738 A1 | 10/2016 | Yoshida et al. | |
| 2016/0310024 A1 | 10/2016 | Yoshida et al. | |
| 2016/0331229 A1 | 11/2016 | Huang et al. | |
| 2017/0112377 A1* | 4/2017 | Shiba | G06T 7/60 |
| 2017/0209037 A1* | 7/2017 | Sumiya | A61B 3/102 |
| 2018/0263492 A1 | 9/2018 | Imamura | |
| 2018/0279874 A1 | 10/2018 | Yoshida et al. | |
| 2018/0338679 A1* | 11/2018 | Schallek | A61B 3/145 |
| 2019/0008377 A1 | 1/2019 | Sumiya | |

FOREIGN PATENT DOCUMENTS

| | | |
|---|---|---|
| JP | 2012-176095 A | 9/2012 |
| JP | 2013-180125 A | 9/2013 |
| JP | 2013-184018 A | 9/2013 |
| JP | 2015-527178 A | 9/2015 |
| JP | 2016-43155 A | 4/2016 |
| JP | 2016-116595 A | 6/2016 |
| JP | 2017-077414 A | 4/2017 |
| JP | 2017-79886 A | 5/2017 |
| JP | 2017-127506 A | 7/2017 |
| JP | 2017-202369 A | 11/2017 |
| JP | 2018-46959 A | 3/2018 |
| WO | 2010/131550 A1 | 11/2010 |

OTHER PUBLICATIONS

Office Action issued Apr. 18, 2023 in Japanese Patent Application No. 2018-246992 and computer-generated English translation thereof, 8 pages.

Office Action issued Aug. 22, 2023 in Japanese Patent Application No. 2018-246992, 4 pages.

Office Action issued Aug. 29, 2023 in Japanese Patent Application No. 2023-005581, 6 pages.

Office Action issued on Oct. 4, 2022, in corresponding Japanese patent Application No. 2018-246992, 8 pages.

Office Action for Japanese Application No. JP 2023-005581, mailed Dec. 26, 2023, 3 pages (machine generated translation attached).

* cited by examiner

BLOOD FLOW MEASUREMENT APPARATUS, METHOD OF CONTROLLING THE SAME, AND RECORDING MEDIUM

CROSS-REFERENCE TO RELATED APPLICATIONS

This application is a national stage (under 35 U.S.C. 371) of International Patent Application No. PCT/JP2019/050980, filed Dec. 25, 2019, claiming priority to Japanese Patent Application No. 2018-246992, filed Dec. 28, 2018, both of which are herein incorporated by reference in their entirety.

TECHNICAL FIELD OF THE INVENTION

The present invention relates generally to a blood flow measurement apparatus used for measuring blood flow dynamics (or hemodynamics) of an eye fundus, a method of controlling the same, and a recording medium.

BACKGROUND OF THE INVENTION

Researches in the field of ophthalmology have been pursuing development of an apparatus for measuring blood flow dynamics of an eye fundus using optical coherence tomography (OCT) (see, for example, Patent Documents 1 and 2 below).

Eye fundus blood flow measurement requires appropriate selection of a measurement position in order to acquire clinically useful data that accurately reflects the actual blood flow dynamics. Furthermore, determination of an appropriate measurement position requires selection of an appropriate blood vessel from among a large number of blood vessels running in the eye fundus, and also requires identification of an appropriate part of the appropriate blood vessel. However, manually performing these tasks is complicated and troublesome for the user, and it is one of the factors that prolongs the time required for examination. In addition, there is a risk that blood flow measurement may be carried out without an appropriate measurement position having been determined.
[PATENT DOCUMENT 1] Japanese Unexamined Patent Application Publication No. 2013-184018
[PATENT DOCUMENT 2] Japanese Unexamined Patent Application Publication No. 2018-46959

BRIEF SUMMARY OF THE INVENTION

An object of the present invention is to automate the process of determining a position for measuring eye fundus blood flow.

A blood flow measurement apparatus of some embodiment examples includes a scanning optical system, a front image acquiring unit, a region-of-interest determining processor, a scan controller, and a blood flow information acquiring unit. The scanning optical system is configured to apply optical coherence tomography (OCT) scanning to a fundus of a subject's eye. The front image acquiring unit is configured to acquire a front image of the fundus. The region-of-interest determining processor is configured to determine a region of interest that intersects a blood vessel by analyzing the front image based on a condition set in advance. The scan controller is configured to control the scanning optical system to apply a repetitive OCT scan to the region of interest. The blood flow information acquiring unit is configured to acquire blood flow information based on data collected by the repetitive OCT scan.

In some embodiment examples, the region-of-interest determining processor includes a blood-vessel-of-interest identifier configured to identify a blood vessel of interest by analyzing the front image based on a blood vessel identification condition set in advance. In addition, the region-of-interest determining processor determines a region of interest that intersects the blood vessel of interest identified.

In some embodiment examples, the blood-vessel-of-interest identifier includes an artery-of-interest identifier configured to identify an artery of interest as the blood vessel of interest.

In some embodiment examples, the blood-vessel-of-interest identifier includes a thick blood vessel identifier configured to identify, as the blood vessel of interest, a thick blood vessel whose diameter is equal to or larger than a threshold value set in advance.

In some embodiment examples, the front image includes an optic nerve head image. Further, the blood-vessel-of-interest identifier identifies, as the blood vessel of interest, a thickest blood vessel for each of two or more regions located in mutually different directions with respect to the optic nerve head image, the thickest blood vessel having a largest diameter in a corresponding region. In addition, the region-of-interest determining processor determines a region of interest that intersects any of two or more thickest blood vessels identified for the two or more regions.

In some embodiment examples, the region-of-interest determining processor includes a position-of-interest identifier configured to identify a position of interest of a blood vessel by analyzing the front image based on a position identification condition set in advance. In addition, the region-of-interest determining processor determines a region of interest that passes through the position of interest identified.

In some embodiment examples, the position-of-interest identifier identifies a position outside a blood vessel branching part as the position of interest.

In some embodiment examples, the position-of-interest identifier identifies a position outside a blood vessel tortuosity part as the position of interest.

In some embodiment examples, the front image includes an optic nerve head image. In addition, the position-of-interest identifier identifies a position away from the optic nerve head image by a predetermined distance as the position of interest.

A method of controlling a blood flow measurement apparatus of some embodiment examples is a method of controlling a blood flow measurement apparatus that measures blood flow dynamics by applying optical coherence tomography (OCT) scanning to a fundus of a subject's eye. The method of controlling such a blood flow measurement apparatus includes a front image acquiring step, a region-of-interest determining step, a scanning step, and a blood flow information acquiring step. The front image acquiring step is configured to acquire a front image of the fundus. The region-of-interest determining step is configured to determine a region of interest that intersects a blood vessel by analyzing the front image based on a condition set in advance. The scanning step is configured to apply a repetitive OCT scan to the region of interest. The blood flow information acquiring step is configured to acquire blood flow information based on data collected by the repetitive OCT scan.

A program of some embodiment examples is configured to cause a blood flow measurement apparatus that includes a computer to execute the method of controlling a blood flow measurement apparatus of some embodiment examples.

A recording medium of some embodiment examples is a computer-readable non-transitory recording medium that records the program of some embodiment examples.

According to some embodiment examples, the process of determining a position for measuring eye fundus blood flow can be automated.

BRIEF SUMMARY OF THE INVENTION

Figure 1:
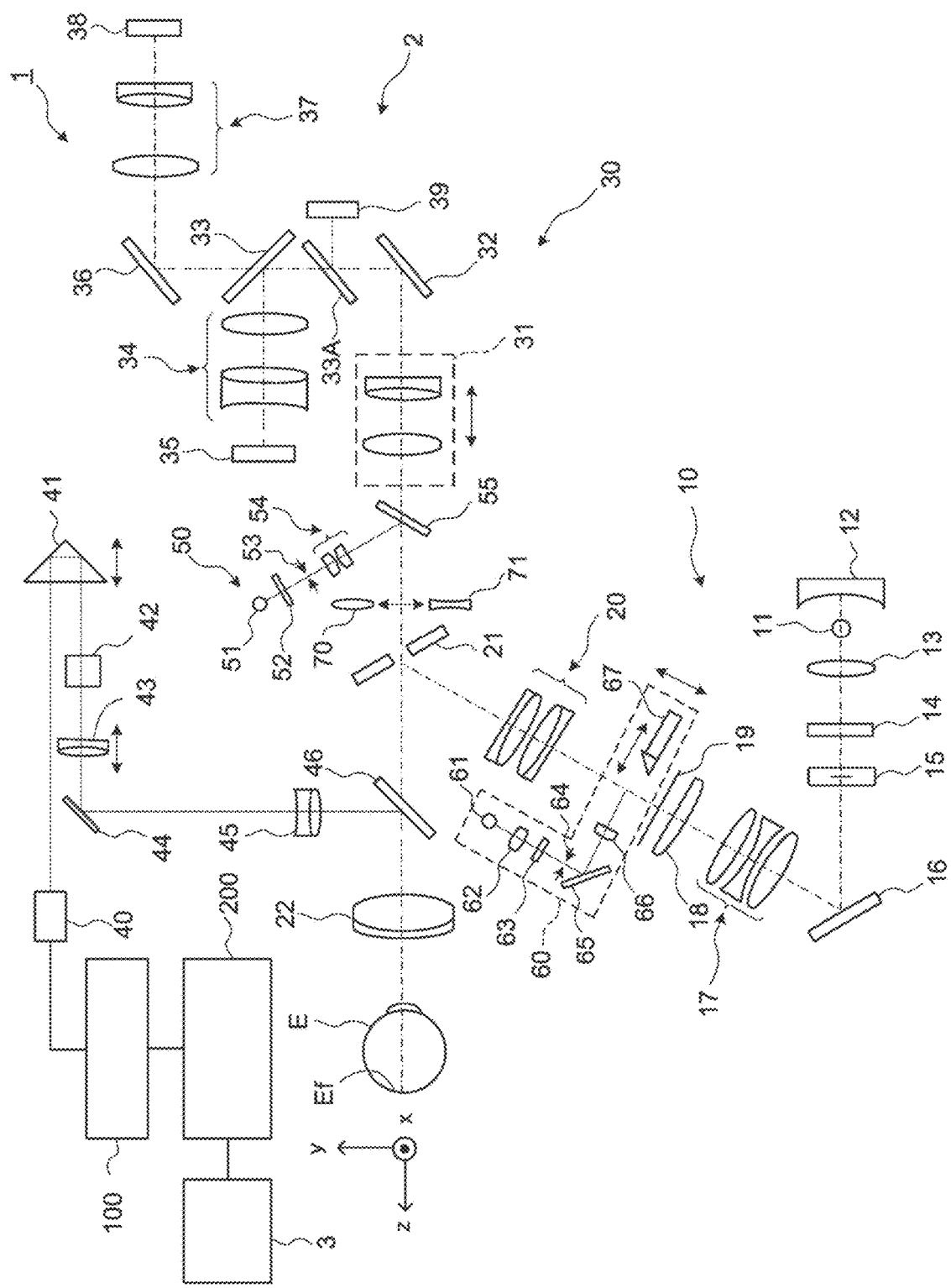
FIG. 1 is a schematic diagram illustrating an example of the configuration of the blood flow measurement apparatus according to the embodiment example.

Some embodiment examples will be described in detail while referring to the drawings. The embodiment examples described below disclose examples of blood flow measurement apparatuses, examples of methods of controlling blood flow measurement apparatuses, examples of programs, and examples of recording media.

A blood flow measurement apparatus according to some embodiment examples is configured to collect data on an eye fundus by OCT scanning and acquire information that represents blood flow dynamics from the collected data (referred to as blood flow information). A blood flow measurement apparatus according to some embodiment examples is capable of measuring the fundus of a living eye utilizing Fourier domain OCT (e.g., swept source OCT). The type of OCT applicable to embodiment examples is not limited to swept source OCT. For example, spectral domain OCT may be applied to some embodiment examples.

Swept source OCT is an imaging technique performed by the following processes: splitting light emitted from a wavelength tunable light source into measurement light and reference light; superposing the reference light with return light of the measurement light returning from the object, thereby generating interference light; detecting the interference light by a balanced photodiode or the like; and applying Fourier transform and other processes to the detection data acquired in synchronization with the wavelength sweeping and the measurement light scanning, thereby constructing an image.

Spectral domain OCT is an imaging technique performed by the following processes: splitting light from a low coherence light source into measurement light and reference light; superposing the reference light with return light of the measurement light returning from the object, thereby generating interference light; detecting the spectral distribution of the interference light using a spectrometer; and applying Fourier transform and other processes to the spectral distribution detected, thereby constructing an image.

As described above, swept source OCT is an OCT technique for acquiring a spectral distribution by time division while spectral domain OCT is an OCT technique for acquiring a spectral distribution by space division. In addition, OCT techniques applicable to embodiment examples are not limited to these two, and some embodiment examples may employ any type of OCT technique different from these two, such as time domain OCT.

A blood flow measurement apparatus according to some embodiment examples may be a multifunctional apparatus configured by combining a fundus imaging apparatus with an OCT apparatus. The fundus imaging apparatus has a function of imaging (photographing) an eye fundus to acquire a front image (digital photograph) thereof. The fundus imaging apparatus thus configured may be a fundus camera (retinal camera) as in the embodiment examples described below, or may be a scanning laser ophthalmoscope (SLO), a slit lamp microscope, an ophthalmic surgical microscope, or another modality.

A blood flow measurement apparatus according to some embodiment examples does not have to have the fundus imaging function. Such a blood flow measurement apparatus has a function of obtaining a front image of an eye fundus from a storage device, a recording medium, or the like. A typical example of the storage device is a medical image archiving system (medical image filing system). Further, typical examples of the recording medium are a hard disk drive and an optical disk.

Any of the contents, items, matters, and the like disclosed in the documents cited in the present specification and any other known techniques and technologies may be incorporated into some embodiment examples. Further, in the present specification, "image data" and an "image" displayed based thereon may not be distinguished from one another unless otherwise mentioned. Likewise, a site or tissue of the subject's eye and an image representing the site or the tissue may not be distinguished from one another unless otherwise mentioned.

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. For example, the processor loads a program stored in a memory circuit or a storage device, and executes the program, thereby implementing a desired function.

<Configuration of Blood Flow Measurement Apparatus>

A description will be given of a blood flow measurement apparatus according to some embodiment examples. The configuration of the illustrative example of the blood flow measurement apparatus is shown in FIG. 1 to FIG. 4B. The blood flow measurement apparatus 1 of the present example includes the fundus camera unit 2, the OCT unit 100, and the arithmetic and control unit 200.

The fundus camera unit 2 is configured to photograph the fundus of a subject's eye to acquire a front image (digital photograph). The fundus camera unit 2 is provided with various kinds of elements (components, parts) for performing digital photography of eye fundi, such as optical elements, actuators, mechanisms, and the like.

The OCT unit 100 is configured to apply swept source OCT scanning to the fundus of the subject's eye to perform data collection (data acquisition). The OCT unit 100 is provided with various kinds of elements (components, parts) for applying OCT scanning to eye fundi, such as optical elements, actuators, mechanisms, and the like. In addition, some elements for applying OCT scanning to fundi are provided in the fundus camera unit 2.

The arithmetic and control unit 200 includes a computer for executing various kinds of operations, calculations, controls, and the like. The computer includes one or more processors.

In addition to the elements (components, parts, units), the blood flow measurement apparatus 1 may also include any elements, units, or the like, such as a member for supporting the face of the subject, a lens unit for switching the sites of the subject's eye to which OCT scanning is applied. The face support member of some embodiment examples may include a chin rest, a forehead rest, or the like. The lens unit of some embodiment examples may include a lens unit for switching the sites subjected to OCT scanning from an eye fundus to an anterior eye segment (attachment for anterior eye segment OCT scanning), a lens unit for switching the sites subjected to OCT scanning from an anterior eye segment to an eye fundus (attachment for eye fundus OCT scanning).

<Fundus Camera Unit 2>

The fundus camera unit 2 includes optical systems and mechanisms for performing digital photography of the fundus Ef of the subject's eye E. examples of digital images of the fundus Ef obtained by the fundus camera unit 2 include front images such as observation images and photographed images. An observation image is obtained by performing moving image photography with near-infrared light. A photographed image is a still image obtained by photography with flash light. Digital images of the fundus Ef obtained by the fundus camera unit 2 may be collectively referred to as "fundus images".

The fundus camera unit 2 includes the illumination optical system 10 and the photography optical system 30. The illumination optical system 10 is configured to project illumination light onto the subject's eye E. The photography optical system 30 is configured to detect return light of the illumination light returning from the subject's eye E. Further, the measurement light entering from the OCT unit 100 is projected onto the subject's eye E through a predetermined route in the fundus camera unit 2, and return light of the measurement light from the subject's eye is directed to the OCT unit 100 through the same route.

The light output from the observation light source 11 of the illumination optical system 10 (referred to as observation illumination light) is reflected by the concave mirror 12, passes through the condenser lens 13, and becomes near-infrared light after passing through the visible cut filter 14.

Then, the observation illumination light is once converged at a location near the photographing light source 15, reflected by the mirror 16, passes through the relay lens system 17, the relay lens 18, the diaphragm 19, and the relay lens system 20. Subsequently, the observation illumination light is reflected on the peripheral part (i.e., the surrounding area of the aperture part) of the aperture mirror 21, penetrates the dichroic mirror 46, and is refracted by the objective lens 22 so as to be projected onto the fundus Ef. As a result of this, the fundus Ef is illuminated by the observation illumination light.

The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Then, the return light of the observation illumination light passes through the half mirror 33A, is reflected by the dichroic mirror 33, and forms an image on the light receiving surface of the image sensor 35 by the condenser lens 34. The image sensor 35 performs detection of the return light of the observation illumination light at a predetermined repetition frequency (frame rate or capture rate). The focus of the photography optical system 30 is adjusted so as to match the fundus Ef in fundus photography. The focus of the photography optical system 30 is adjusted so as to match the anterior eye segment in anterior eye segment photography.

The light output from the photographing light source 15 (referred to as photographing illumination light) passes through the same route as that of the observation illumination light and is projected onto the fundus Ef. Return light of the photographing illumination light returning from the fundus Ef passes through the same route as that of the return light of the observation illumination light so as to be guided to the dichroic mirror 33. Then, the return light of the photographing illumination light passes through the dichroic mirror 33, is reflected by the mirror 36, and forms an image on the light receiving surface of the image sensor 38 by the condenser lens 37.

The liquid crystal display (LCD) 39 displays a fixation target (fixation target image). Part of a light beam output from the LCD 39 is reflected by the half mirror 33A, reflected by the mirror 32, travels through the photography focusing lens 31 and the dichroic mirror 55, and passes through the aperture part of the aperture mirror 21. Then, the light beam penetrates the dichroic mirror 46, and is refracted by the objective lens 22 so as to be projected onto the fundus Ef.

Changing the display position of the fixation target image on the screen of the LCD 39 allows the direction (orientation) of the line of sight (fixation position) of the subject's eye E guided by the fixation target to be varied. Examples of the fixation position includes the followings: a fixation position for acquiring an image centered on the macula of an eye fundus; a fixation position for acquiring an image centered on the optic nerve head; a fixation position for acquiring an image centered on the fundus center that is located between the macula and the optic nerve head; and a fixation position for acquiring an image of a site far away from the macula (periphery of an eye fundus).

Some embodiment examples may be provided with a user interface that can be used for designating at least one of typical fixation positions like the above examples. Further, some embodiment examples may be provided with a user interface that can be used for manually changing the fixation position (i.e., the display position of the fixation target).

The element for presenting fixation targets to the subject's eye E is not limited to display devices such as an LCD. For example, a fixation matrix device may be adopted in place of a display device in some embodiment examples. The fixation matrix device includes a plurality of light emitting elements (e.g., light emitting diodes) that are disposed in a matrix-like arrangement (in a matrix array). In some embodiment examples, the fixation positions may be changed by lighting one (or more) of the plurality of light emitting elements in a selective manner. As another example, the fixation target usable for fixation position change may be generated by employing one or more movable light emitting elements. Each light emitting element of this example is, for example, a light source such as a light emitting diode (LED).

The alignment optical system 50 generates an alignment indicator used for alignment operations of the optical system with respect to the subject's eye E. Alignment light output from the LED 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light returning from the subject's eye E passes through the same route as that of the return light of the observation illumination light so as to be guided to the image sensor 35. On the basis of an image of the return light of the alignment light detected by the image sensor 35 (referred to as an alignment indicator image), either one or both of manually operated alignment and automatically operated alignment may be performed.

The alignment indicator image of the present example includes two bright spot images whose positions change depending on alignment states. When the relative position between the subject's eye E and the optical system shifts in a certain direction in the xy plane, the positions of the two bright spot images integrally shift in the direction corresponding to the shift direction of the relative position. When the relative position between the subject's eye E and the optical system shifts in a direction along the z coordinate axis, the relative position (distance) between the two bright spot images changes in the direction corresponding to the direction along the z coordinate axis. When the distance between the subject's eye E and the optical system in the z direction matches working distance determined in advance, the two bright spot images overlap with each other. When the position of the subject's eye E matches the position of the optical system in the xy direction, the two bright spot images are presented within a given alignment target. The position of the optical system with respect to the subject's eye E is adjusted so that these two conditions are satisfied.

For the automatically operated alignment, the data processor 230 detects the positions of the two bright spot images, and the main controller 211 determines movement direction and movement amount of the optical system based on the positional relationship between the two bright spot images and the alignment target. Based on the movement direction and the movement amount determined, the main controller 211 executes control of the movement mechanism 150. In the manually operated alignment, the main controller 211 displays on the display 241 an observation image of the subject's eye E in which the two bright spot images are depicted, and the user carries out operations for moving the optical system using the operation device 242 while referring to the two bright spot images being displayed.

The focus optical system 60 generates a split indicator used for focus adjustment operations with respect to subject's eye E. The focus optical system 60 is moved along the optical path of the illumination optical system 10 (referred to as an illumination optical path) in conjunction with the movement of the photography focusing lens 31 along the optical path of the photography optical system 30 (referred to as a photographing optical path). Prior to focus adjustment operation, the reflection rod 67 is inserted into the illumination optical path, and the reflective surface of the reflection rod 67 is arranged in the slanted state with respect to the illumination optical path.

Focus light output from the LED 61 passes through the relay lens 62, is split into two light beams by the split indicator plate 63, passes through the two-hole diaphragm 64. Then, the focus light is reflected by the mirror 65, is converged on the reflective surface of the reflection rod 67 by the condenser lens 66, and is reflected by the reflective surface. Subsequently, the focus light travels through the relay lens 20, is reflected by the aperture mirror 21, and penetrates the dichroic mirror 46, thereby being projected onto the subject's eye E via the objective lens 22. Return light of the focus light returning from the subject's eye E passes through the same route as that of the return light of the alignment light and is guided to the image sensor 35. Based on an image of the return light of the focus light detected by the image sensor 35 (referred to as a split indicator image), either one or both of manually operated focusing and automatically operated focusing are performed.

The diopter correction lenses 70 and 71 are selectively placed at a position between the aperture mirror 21 and the dichroic mirror 55 (i.e., a position in the photographing optical path). The diopter correction lens 70 is a positive lens (convex lens) for correcting high hyperopia. The diopter correction lens 71 is a negative lens (concave lens) for correcting high myopia.

The dichroic mirror 46 couples the fundus photography optical path (i.e., the illumination optical path and the photographing optical path) and the OCT optical path (i.e., the measurement arm). The dichroic mirror 46 reflects the wavelength bands of the OCT measurement light while passing the wavelength bands of the fundus photography light. The measurement arm is formed by elements including, listed from the OCT unit 100 side, the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 1 so as to change the length of the measurement arm. The change in the length of the measurement arm can be utilized for operations such as optical path length correction based on axial length and interference condition adjustment, for example.

The dispersion compensation member 42 functions to eliminate the difference between the dispersion characteristics of the measurement arm and that of the reference arm, together with the dispersion compensation member 113 arranged in the reference arm.

The OCT focusing lens 43 is moved along the measurement arm in order to perform the focus adjustment of the measurement arm. Note that the movement of the photography focusing lens 31, the movement of the focus optical system 60, and the movement of the OCT focusing lens 43 may be controlled to be performed in an interlocking manner.

The optical scanner 44 is placed at a position substantially optically conjugate with respect to the pupil of the subject's eye E. The optical scanner 44 is configured to deflect the measurement light LS guided by the measurement arm. An example of the optical scanner 44 is provided by a galvano scanner configured to be capable of two dimensional scanning. Typically, the galvano scanner includes an x-scanner for deflecting the measurement light in the x direction and a y-scanner for deflecting the measurement light in they direction. If this is the case, the pupil conjugate position may be designed to be located at, for example, any one of the position of the reflective surface of the x-scanner, the position of the reflective surface of the y-scanner, and a position between the x-scanner and the y-scanner.

<OCT Unit 100>

Figure 2:
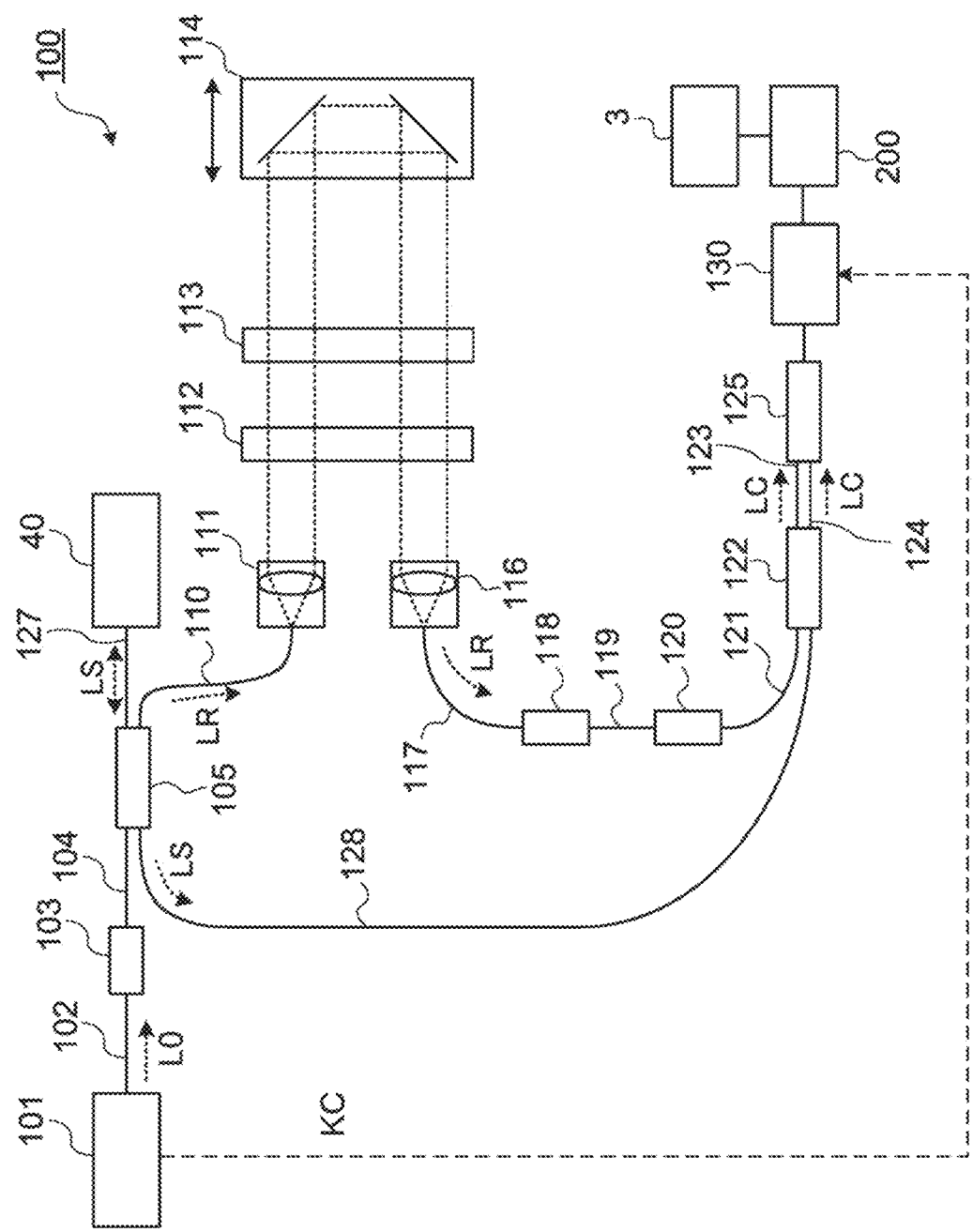
FIG. 2 is a schematic diagram illustrating an example of the configuration of the blood flow measurement apparatus according to the embodiment example.

As illustrated in FIG. 2, the OCT unit 100 is provided with the elements for performing swept source OCT scanning. The OCT unit 100 includes an interference optical system. The interference optical system is configured to split light emitted from a wavelength tunable light source into measurement light and reference light, superpose the reference light with return light of the measurement light returning from the subject's eye E so as to yield interference light, and then detect the interference light. A result of the detection (i.e., detection signal) of the interference light is a signal representing the spectrum of the interference light, and is sent to the arithmetic and control unit 200.

The light source unit 101 includes, as an example of a tunable light source, a near-infrared wavelength tunable laser configured to be capable of changing emission wavelengths at high speed. The light L0 output from the light source unit 101 is guided to the polarization controller 103 through the optical fiber 102, and the polarization state (polarization condition) of the light L0 is regulated by the polarization controller 103. Further, the light L0 with regulated polarization state is guided to the fiber coupler 105 through the optical fiber 104, and is split into the measurement light LS and the reference light LR by the fiber coupler 105. In the present specification, the optical path of the measurement light LS is referred to as the measurement arm, and the optical path of the reference light LR is referred to as the reference arm.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 functions to compensate for the difference between the length of the reference arm and the length of the measurement arm. The dispersion compensation member 113 functions to eliminate the difference between the dispersion characteristics of the reference arm and that of the measurement arm with each other, together with the dispersion compensation member 42 arranged in the measurement arm. The retroreflector 114 is movable along the incident direction of the reference light LR with respect to the retroreflector 114, that is, along the direction in which the reference light LR travels away from the retroreflector 114. The movement of the retroreflector 114 allows the length of the reference arm to be changed. The change in the length of the reference arm may be utilized for operations such as optical path length correction based on axial length and interference condition adjustment.

Note that while the present embodiment example is provided with both the element for changing the length of the measurement arm (e.g., the retroreflector 41) and the element for changing the length of the reference arm (e.g., the retroreflector 114 or a reference mirror), some embodiment examples may be provided with only any one of these two elements. Further, elements for changing the difference between the length of the measurement arm and the length of the reference arm (referred to as optical path length difference) are not limited to the elements described above, and may be any kind of element such as an optical member, a mechanism, or the like.

After reflected by the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization controller 118. The polarization state of the reference light LR is regulated by the polarization controller 118. Then, the reference light LR is guided to the attenuator 120 through the optical fiber 119. The light amount of the reference light LR is regulated by the attenuator 120. Subsequently, the reference light LR is guided to the fiber coupler 122 through the optical fiber 121.

Meanwhile, the measurement light LS generated by the fiber coupler 105 is guided to the collimator lens unit 40 through the optical fiber 127. The measurement light LS is converted to a parallel light beam by the collimator lens unit 40. Then, the measurement light LS travels via the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depths of the subject's eye E. Return light of the measurement light LS returning from the subject's eye E travels through the same route as the outward way in the opposite direction so as to be directed to the fiber coupler 105, and then reaches the fiber coupler 122 through the optical fiber 128.

The fiber coupler 122 superposes the measurement light LS incident through the optical fiber 128 with the reference light LR incident through the optical fiber 121. The superposition generates interference light. The fiber coupler 122 splits the generated interference light at a predetermined ratio (e.g., 1 to 1) so as to generate a pair of interference light LC. The pair of interference light LC is guided to the detector 125 through the optical fibers 123 and 124, respectively.

The detector 125 includes, for example, a balanced photo diode. The balanced photodiode includes a pair of photodetectors. The pair of photodetectors respectively detects the pair of the interference light LC. The balanced photodiode outputs a difference signal between a pair of output signals respectively from the pair of photodetectors. The detector 125 transmits the difference signal (i.e., detection signal) to the data acquisition system (DAQ) 130.

The clock KC is supplied from the light source unit 101 to the data acquisition system 130. The clock KC is generated in the light source unit 101 in synchronization with the output timings of respective wavelengths varied over a predetermined wavelength range by the wavelength tunable type light source. For this purpose, the light source unit 101 of some embodiment examples includes the following elements: an element configured to split the light L0 of each output wavelength to generate two pieces of split light; an element configured to apply an optical delay to one of the two pieces of split light; an element configured to combine the resulting two pieces of split light (one of the two has been subjected to optical delay) to generate combined light; an element configured to detect the combined light generated; and an element configured to generate the clock KC from the detection result of the combined light. The data acquisition system 130 performs sampling of the detection signal input from the detector 125 based on the clock KC. The data acquisition system 130 transmits the result of the sampling of the detection signal to the arithmetic and control unit 200.

<Processing System>

Figure 3:
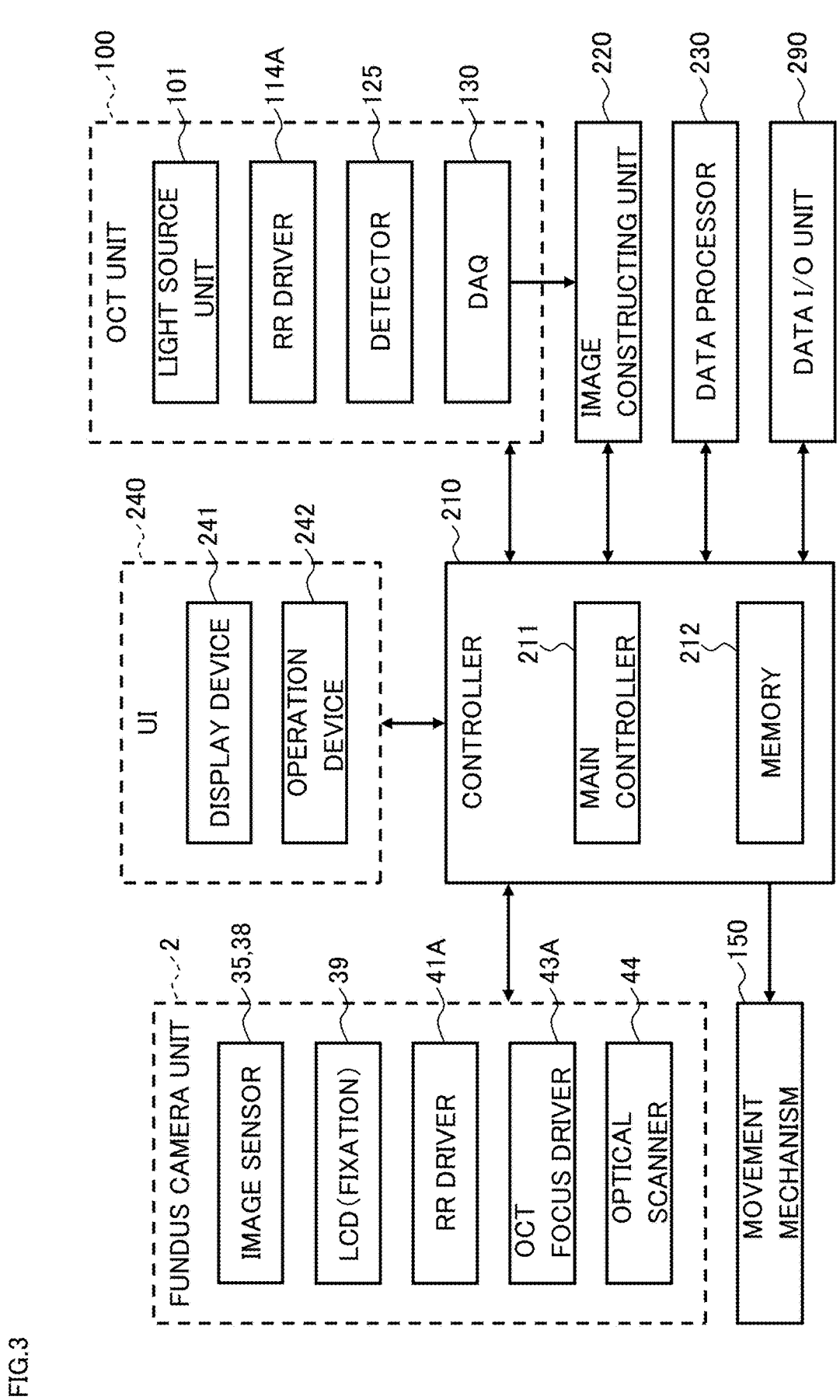
FIG. 3 is a schematic diagram illustrating an example of the configuration of the blood flow measurement apparatus according to the embodiment example.
Figure 4A:
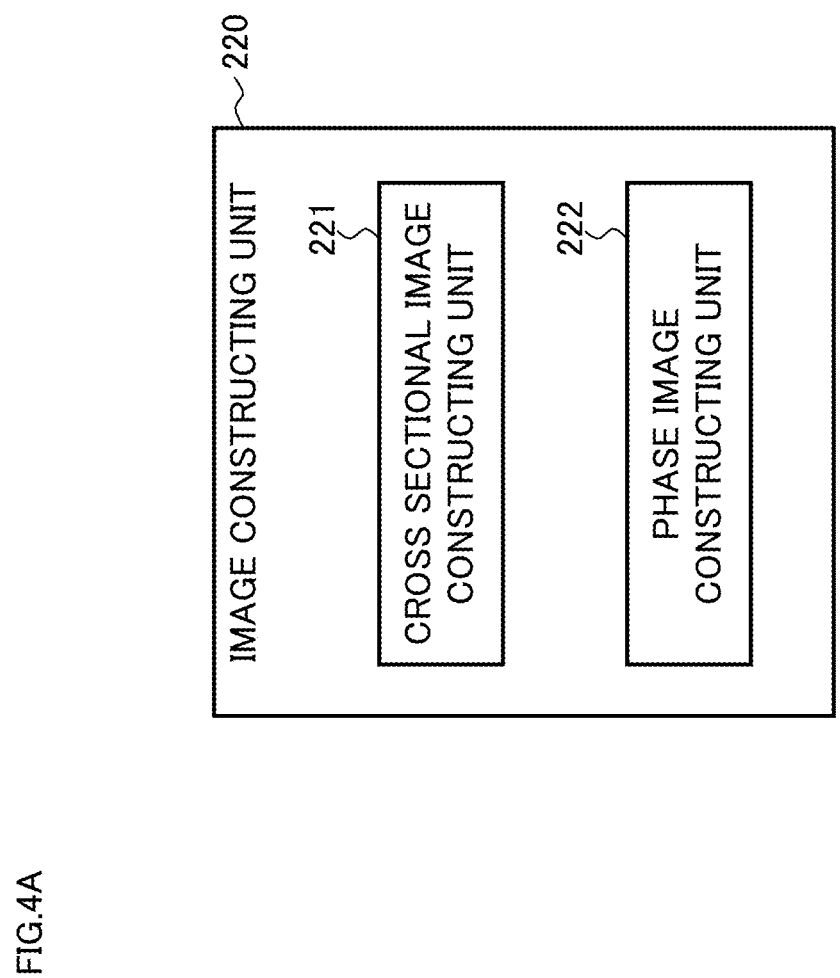
FIG. 4A is a schematic diagram illustrating an example of the configuration of the blood flow measurement apparatus according to the embodiment example.
Figure 4B:
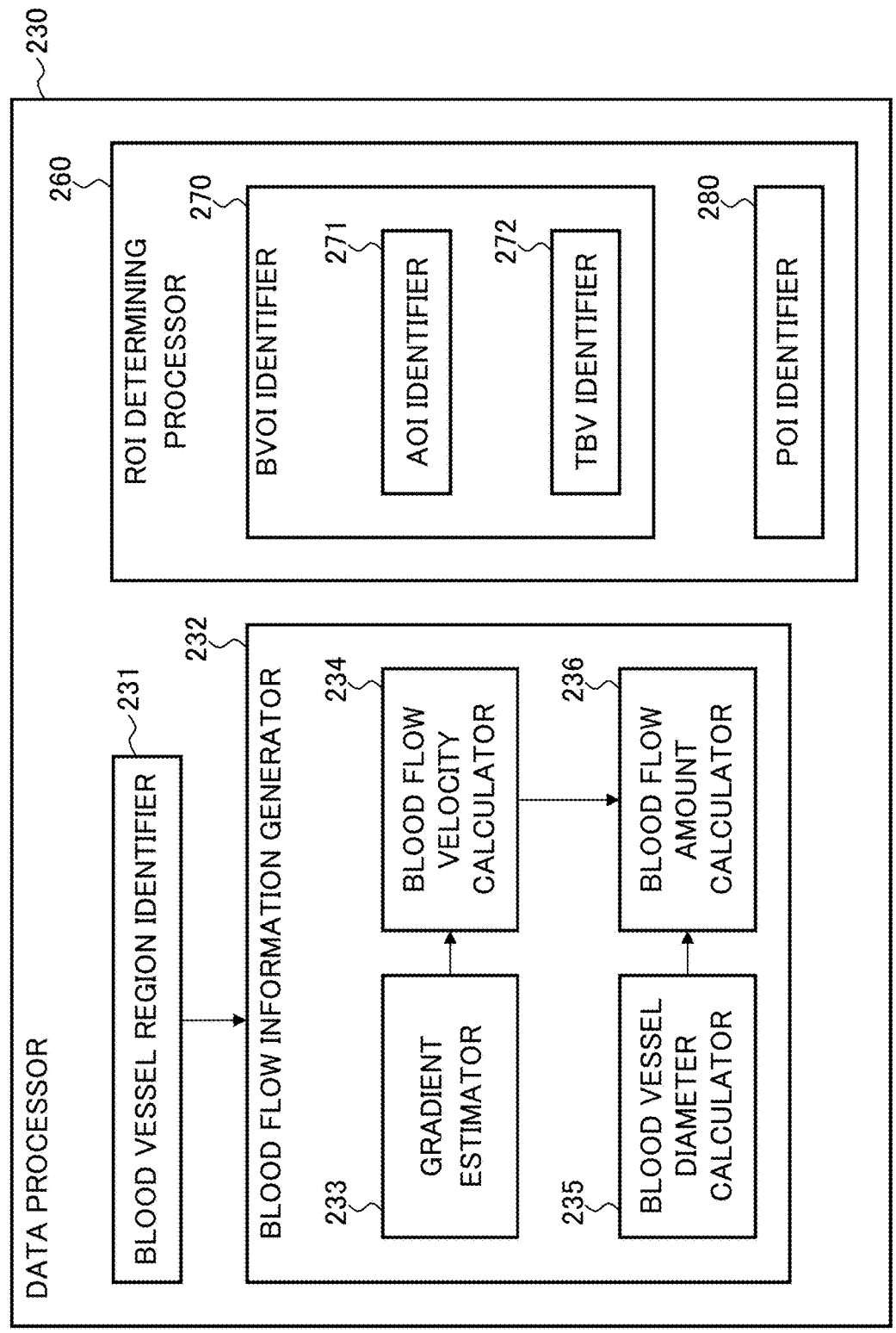
FIG. 4B is a schematic diagram illustrating an example of the configuration of the blood flow measurement apparatus according to the embodiment example.

FIG. 3, FIG. 4A and FIG. 4B show an example of the configuration of the processing system (arithmetic and control system) of the blood flow measurement apparatus 1. The controller 210, the image constructing unit 220 and the data processor 230 may be provided in the arithmetic and control unit 200.

<Controller 210>

The controller 210 performs various kinds of controls. The controller 210 includes the main controller 211 and the memory 212.

<Main Controller 211>

The main controller 211 includes a processor that can be operated based on a control program, and executes control of each part (element, unit) of the blood flow measurement apparatus 1 (including the units and elements shown in FIG. 1 to FIG. 4B).

The photography focusing lens 31 disposed in the photographing optical path and the focus optical system 60 disposed in the illumination optical path are moved in a synchronized manner by a photographing focus driver (not shown) under the control of the main controller 211. The retroreflector 41 disposed in the measurement arm is moved by the retroreflector driver (RR driver) 41A under the control of the main controller 211. The OCT focusing lens 43 disposed in the measurement arm is moved by the OCT focus driver 43A under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211.

The movement mechanism 150 moves, for example, at least the fundus camera unit 2 in a three dimensional manner. In a typical example, the movement mechanism 150 includes the followings: an x-stage movable in the +x and −x directions (left and right directions); an x-movement mechanism that moves the x-stage; a y-stage movable in the +y and −y directions (up and down directions, vertical direction); a y-movement mechanism that moves the y-stage; a z-stage movable in the +z and −z directions (depth direction, front and back directions); and a z-movement mechanism that moves the z-stage. Each of the movement mechanisms described here includes an actuator such as a pulse motor that operates under control of the main controller 211.

<Memory 212>

The memory 212 stores various kinds of data. Examples of the data stored in the memory 212 include OCT images, fundus images, and subject's eye information. The subject's eye information includes subject information such as the patient ID and the patient's name, identification information for the left eye and the right eye, and electronic medical record information.

The memory 212 stores information for performing determination of a location to which an OCT scan for eye fundus blood flow dynamics measurement is applied. The location is referred to as a region of interest (ROI). The region of interest is determined in such a manner as to intersect a blood vessel that satisfies a predetermined first condition. In addition, the region of interest is determined in such a manner as to intersect the blood vessel at a location that satisfies a predetermined second condition.

The first condition is a condition for identifying a blood vessel to which an OCT scan for eye fundus blood flow dynamics measurement is applied. Hereinafter, the first condition is referred to as a blood vessel identification condition. A blood vessel identified on the basis of the blood vessel identification condition is referred to as a blood vessel of interest.

The blood vessel identification condition of some embodiment examples may include any one or more of the following conditions: a condition relating to the type of a blood vessel (referred to as a blood vessel type condition); a condition relating to the thickness of a blood vessel (referred to as a blood vessel diameter condition); and a condition relating to the position or location of a blood vessel (referred to as a blood vessel position condition). Note that the blood vessel identification condition of some embodiment examples may include conditions other than these examples.

It is considered desirable that a blood vessel (or a candidate blood vessel) to which an OCT scan for eye fundus blood flow dynamics measurement is to be applied, is an artery for which a temporal change (temporal variation, chronological change, chronological variation, time course) in the blood flow dynamics appears relatively remarkably. The blood vessel type condition of some embodiment examples includes a condition for identifying an artery, and typically includes a condition for discriminating (separating) arteries from veins.

With reference to conditions and processes of identifying an artery, for example, the techniques or technologies disclosed by the present applicant in any of the following documents may be used: Japanese Unexamined Patent Application Publication No. 2007-319403; Japanese Unexamined Patent Application Publication No. 2016-043155; Japanese Unexamined Patent Application Publication No. 2016-116595; Japanese Unexamined Patent Application Publication No. 2017-079886; Japanese Unexamined Patent Application Publication No. 2017-202369; Japanese Unexamined Patent Application Publication No. 2018-046959. Some embodiment examples may be configured to perform artery identification by employing an image processing technique or technology other than those disclosed in the documents listed above, an artificial intelligence technique or technology, a cognitive computing technique or technology, or the like. In the case of utilizing an artificial intelligence technique or technology or a cognitive computing technique or technology, the blood vessel type condition may include a set of parameters of a multilayer neural network to which deep learning has been applied, for example.

It is considered desirable that a blood vessel (or a candidate blood vessel) to which an OCT scan for eye fundus blood flow dynamics measurement is to be applied, has a certain degree of thickness or greater. An example of the blood vessel diameter condition may include a threshold value (lower limit) for blood vessel diameter. The threshold value may be set to 100 micrometers, for example. The blood vessel diameter may be the diameter of the outer wall of a blood vessel or the diameter of the inner wall of a blood vessel.

In regard to processing for blood vessel diameter calculation, for example, the technique or technology disclosed by the present applicant in Japanese Unexamined Patent Application Publication No. 2016-43155 may be employed. A typical example of the blood vessel diameter calculation may include the following processes: a process of identifying a blood vessel wall image (e.g., a blood vessel outer wall image, or a blood vessel inner wall image) from a front image of an eye fundus; a process of acquiring blood vessel running information (e.g., a blood vessel axis line, a blood vessel center line, a blood vessel wall image, or the like); a process of identifying a blood vessel width direction (e.g., a direction orthogonal to the blood vessel axis line) from the blood vessel running information; a process of identifying intersection points of a straight line along the blood vessel width direction and the two blood vessel wall images; and a process of calculating the distance between the two intersection points identified. The distance thus calculated corresponds to the blood vessel diameter at the measurement position (measurement location) concerned.

In order to improve the suitability of eye fundus blood flow dynamics measurement (improvement of the precision, improvement of the accuracy, improvement of the efficiency, and the like), the position or location in an eye fundus of a blood vessel (or a candidate blood vessel) to which an OCT scan is to be applied may be added to the conditions. An example of the blood vessel position condition may include information that defines the position (of the blood vessel) with respect to a feature point of an eye fundus. Typically, the blood vessel position condition may include a condition indicating two or more regions that are located in different directions from each other with respect to an optic nerve head. As an example, the blood vessel position condition may include a condition indicating four quadrants defined with respect to the center (or the center of gravity) of an optic nerve head as the origin, and may further include a condition for identifying the blood vessel having the largest diameter (referred to as the thickest blood vessel) in each of the four quadrants.

Regarding processing for identifying the center (or the center of gravity) of an optic nerve head, for example, the technique or technology disclosed by the present applicant in Japanese Unexamined Patent Application Publication No. 2008-206684 may be applied. A typical optic nerve head identification processing may include the following processes: a process of identifying an optic nerve head image from a front image of the fundus (here, the optic nerve head image may be an image region corresponding to the edge of the optic nerve head); a process of determining a circle (or an ellipse) that approximates the edge of the optic nerve head image; and a process of determining the center of the approximate circle (or the approximate ellipse) determined.

Processing of determining the four quadrants whose origin is the center of the optic nerve head may include the following processes, for example: a process of identifying a reference direction; and a process of determining four quadrants based on the reference direction identified. The reference direction may be any one of a direction defined based on the frame of a front image of an eye fundus and a direction defined based on a feature point of an eye fundus. The former direction may be, for example, a direction defined by the coordinate axes preset in the image frame, and is typically any one of the x direction and the y direction. The latter direction may be, for example, a direction defined based on the straight line passing through the center of the optic nerve head and the center of the macula (fovea centralis). It should be noted that processing of identifying the fovea centralis may be performed in the same manner as processing of identifying the center of the optic nerve head. The four quadrants may be defined, for example, based on the following straight lines: a straight line arranged along the reference direction that passes through the center of the optic nerve head; and the straight line that is perpendicular to the straight line arranged along the reference direction and that passes through the center of the optic nerve head.

The second condition is a condition for identifying an application position of an OCT scan for measuring the blood flow dynamics of an eye fundus. Hereinafter, the second condition is referred to as a position identification condition. A position of a blood vessel identified on the basis of the position identification condition is referred to as a position of interest.

The position identification condition may include, for example, any one or more of the following conditions: a condition relating to branching of a blood vessel (referred to as a branching condition); a condition relating to tortuosity of a blood vessel (referred to as a tortuosity condition); and a condition relating to a position with respect to a site of an eye fundus (referred to as a relative position condition). Note that the position identification condition may include a condition other than the above examples.

In order to perform eye fundus blood flow dynamics measurement with high reliability (e.g., with high precision and high accuracy), it is considered desirable to apply an OCT scan avoiding a blood vessel branching part and vicinity thereof at which blood flow dynamics is complex. An example of the branching condition includes a threshold value for a distance from a blood vessel branching part.

The identification of a blood vessel branching part may include, for example, the following processes: a process of acquiring blood vessel running information (e.g., a blood vessel axis line, a blood vessel center line, a blood vessel wall image, etc.) from a front image of an eye fundus; and a process of identifying a blood vessel branching part on the basis of the blood vessel running information. The blood vessel branching part can be identified, for example, as a branching point of a blood vessel axis (blood vessel center line) or as a figure (e.g., a triangle or a circle) surrounding a branching point. The distance from the blood vessel branching part may be defined, for example, as the distance from the branching point or from the figure.

In order to perform eye fundus blood flow dynamics measurement with high reliability, it is considered desirable to apply an OCT scan avoiding a blood vessel tortuosity part and vicinity thereof at which blood flow dynamics is complex. An example of the tortuosity condition includes a threshold value for the curvature radius (or curvature) of a blood vessel.

The identification of a blood vessel tortuosity part may include, for example, the following processes: a process of acquiring blood vessel running information (e.g., a blood vessel axis line, a blood vessel center line, a blood vessel wall image, etc.) from a front image of an eye fundus; a process of calculating the curvature radius of a blood vessel (e.g., the curvature radius at each point of a blood vessel axis line) from the blood vessel running information; and a process of identifying a position at which the curvature radius is greater than a threshold value (i.e., a process of identifying a position where the bending (or curve) of a blood vessel is relatively mild (or moderate)).

In order to perform eye fundus blood flow dynamics measurement with high reliability, it is considered desirable to apply an OCT scan to an appropriate position on an eye fundus. For example, considering the morphology (or structure) of the blood vessel network (or vascular network) that supplies blood to an eye fundus, it may be desirable to apply an OCT scan to a blood vessel located at a position where a specific condition (relative position condition) with respect to the optic nerve head is satisfied.

In the blood vessel network that supplies blood to an eye fundus, blood flows into the eye fundus through arteries that pass through the optic nerve head. Further, the blood that has been transported to various parts of the eye fundus through the arteries flows into veins through capillaries, and the blood is transported through the veins to the optic nerve head. Then, the blood flows out of the eye fundus through the veins that pass through the optic nerve head. In addition, the bending (or curve) of blood vessels is relatively large at and near the edge of the optic nerve head, and blood vessels in the vicinity of the optic nerve head are relatively thick. Taking these factors (facts) into consideration, a position some distance away from the optic nerve head is considered to be an appropriate position for applying an OCT scan. For example, a position away from the edge of the optic nerve head by a distance equal to the diameter of the optic nerve head may be employed as an application position of an OCT scan.

<Image Constructing Unit 220>

The image constructing unit 220 is configured to construct OCT image data of the fundus Ef based on the signal (sampling data, or sampled data) input from the data acquisition system 130. The image constructing unit 220 may construct B-scan image data (i.e., two dimensional cross sectional image data) and phase image data of the fundus Ef. These pieces of OCT image data will be described later. The image constructing unit 220 includes, for example, a processor operable in accordance with an image constructing program.

The blood flow measurement of the present embodiment performs two types of scans on the fundus Ef. The two types of scans will be referred to as a main scan and a supplementary scan.

The main scan performs repetitive scanning with the measurement light LS on a region of interest that intersects a blood vessel of interest of the fundus Ef at a position of interest, so as to acquire phase image data. Such a region of interest to which the main scan is applied is referred to as a cross section of interest.

The supplementary scan performs a scan on a predetermined cross section with the measurement light LS in order to estimate the gradient (or, inclination, tilt, slope, slant, or the like) of the blood vessel of interest at the cross section of interest. The cross section to which the supplementary scan is applied is referred to as a supplementary cross section. In some examples, the supplementary cross section may be a cross section that intersects the blood vessel of interest and is located in the vicinity of the cross section of interest. Such a supplementary cross section is referred to as the first supplementary cross section. In some other examples, the supplementary cross section may be a cross section that intersects the cross section of interest and is oriented along the blood vessel of interest. Such a supplementary cross section is referred to as the second supplementary cross section.

Figure 5A:
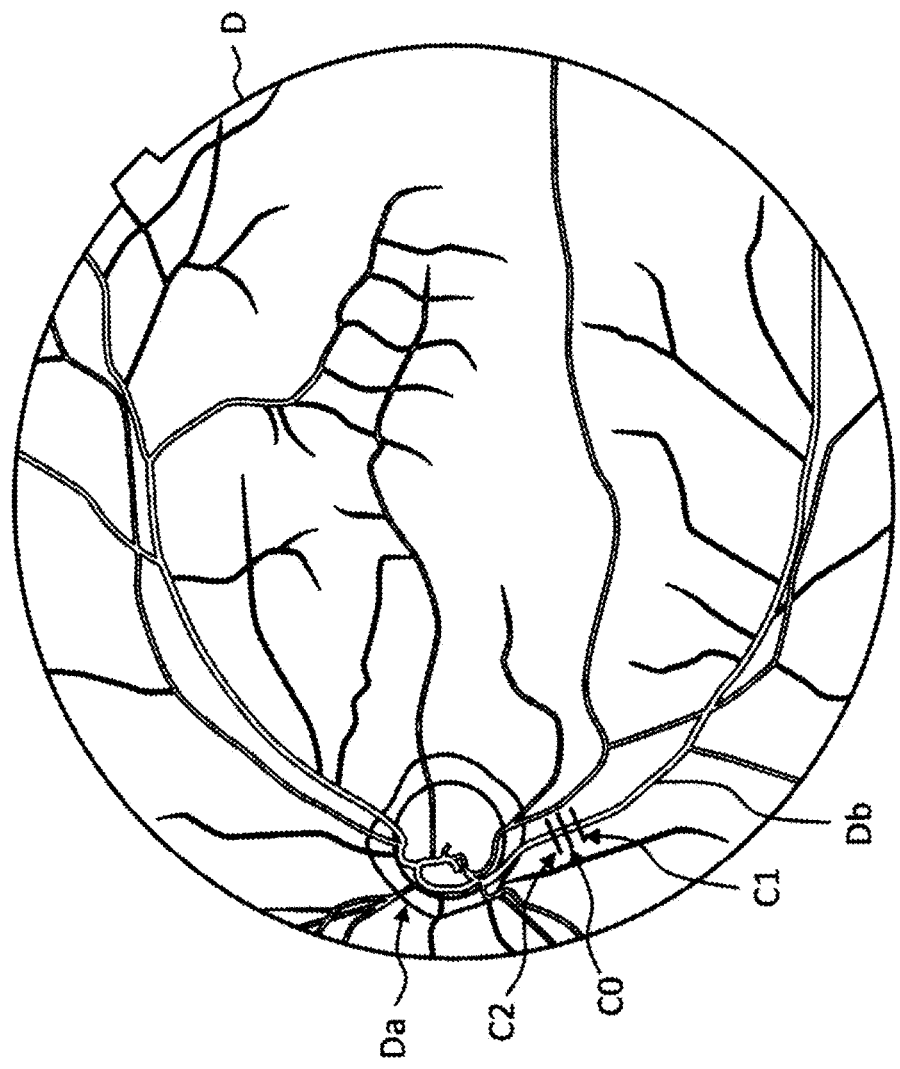
FIG. 5A is a schematic diagram for describing an example of the operation of the blood flow measurement apparatus according to the embodiment example.

FIG. 5A shows an example in which the first supplementary cross section is employed. In the present example, as shown on the fundus image D, one cross section of interest C0 and two supplementary cross sections C1 and C2 are set to intersect the blood vessel of interest Db. Here, the cross section of interest C0 is located near the optic nerve head Da of the fundus Ef, and the supplementary cross sections C1 and C2 are located near the cross section of interest C0. One of the two supplementary cross sections C1 and C2 is located on the upstream side of the blood vessel of interest Db with respect to the cross section of interest C0, and the other is located on the downstream side. The cross section of interest C0 and the supplementary cross sections C1 and C2 are each oriented to be substantially orthogonal to the running direction of the blood vessel of interest Db, for example.

Figure 5B:
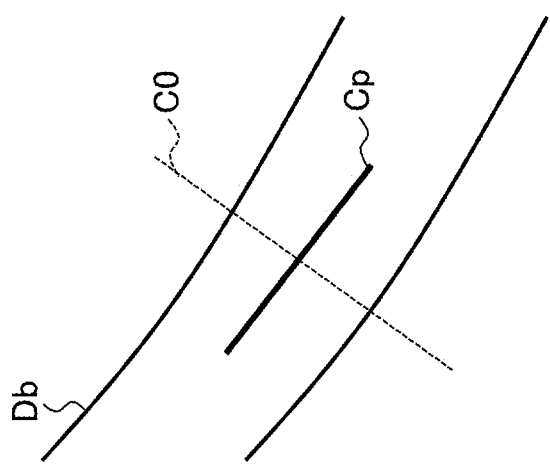
FIG. 5B is a schematic diagram for describing an example of the operation of the blood flow measurement apparatus according to the embodiment example.

FIG. 5B shows an example in which the second supplementary cross section is employed. Similar to the above example shown in FIG. 5A, the cross section of interest C0 is set to be substantially orthogonal to the blood vessel of interest Db in the present example. Further, in the present example, the supplementary cross section Cp is set to be substantially orthogonal to the cross section of interest C0. The supplementary cross section Cp is oriented along the blood vessel of interest Db. As an example, the supplementary cross section Cp may be set to pass through the intersection between the central line of the blood vessel of interest Db and the cross section of interest C0.

In some examples of blood flow measurement, the main scan performs repetitive scanning over a period of time containing at least one cardiac cycle of the patient's heart. This makes it possible to obtain blood flow dynamics information for all cardiac phases. The period of time during which the main scan is performed may be a fixed length of time set in advance, or a length of time set for a target patient or an examination to be conducted. In the former case (fixed length of time), a period of time longer than the standard cardiac cycle is set (e.g., 2 seconds). In the latter case (non-fixed length of time), biometric data (medical parameters) such as the patient's electrocardiogram may be referred to. Here, any factor other than cardiac cycles may be considered. Examples of such factors include the length of time required for conduction of examination (e.g., burden on patients), the response time of the optical scanner 44 (e.g., scanning time interval), the response time of the detector 125 (e.g., scanning time interval), and the like.

The image constructing unit 220 includes the cross sectional image constructing unit 221 and the phase image constructing unit 222. The cross sectional image constructing unit 221 includes, for example, a processor operable in accordance with a cross sectional image constructing program. The phase image constructing unit 222 includes, for example, a processor operable in accordance with a phase image constructing program.

<Cross Sectional Image Constructing Unit 221>

The cross sectional image constructing unit 221 is configured to construct cross sectional images that represent a temporal change (or, temporal variation, chronological change, chronological variation, time course, or the like) in the morphology (or structure) of the cross section of interest, based on sampling data obtained by the data acquisition system 130 with the main scan. Such a cross sectional image is referred to as a main cross sectional image. This cross sectional image construction process will be described in more detail. As described above, the main scan performs repetitive scanning on the cross section of interest C0. Sampling data is sequentially input from the data acquisition system 130 to the cross sectional image constructing unit 221 in response to the repetition of scans. The cross sectional image constructing unit 221 constructs one main cross sectional image corresponding to the cross section of interest C0, based on the sampling data corresponding to one scan performed on the cross section of interest C0. The cross sectional image constructing unit 221 repeats such processing as many times as the number of repetition of scans in the main scan, to construct a series of main cross sectional images in time series. Here, these main cross sectional images may be put into a plurality of groups, and then two or more main cross sectional images belonging to one group may be synthesized or composed to create an image having improved image quality. Such processes are referred to as image averaging.

Further, the cross sectional image constructing unit 221 constructs a cross sectional image that represents the morphology (or structure) of the supplementary cross section, based on sampling data obtained by the data acquisition system 130 with the supplementary scan for the supplementary cross section(s). Such a cross sectional image is referred to as a supplementary cross sectional image. The supplementary cross sectional image constructing process may be executed in the same manner as the main cross sectional image constructing process described above. Here, the main cross sectional image is a series of cross sectional images in time series, but the supplementary cross sectional image may be one cross sectional image. Further, the supplementary cross sectional image may be an image having improved image quality created by synthesizing or composing a plurality of cross sectional images acquired by a plurality of scans on the supplementary cross section (image averaging).

When the supplementary cross sections C1 and C2 illustrated in FIG. 5A are employed, the cross sectional image constructing unit 221 constructs a supplementary cross sectional image corresponding to the supplementary cross section C1 and a supplementary cross sectional image corresponding to the supplementary cross section C2. On the other hand, when the supplementary cross section Cp illustrated in FIG. 5B is employed, the cross sectional image constructing unit 221 constructs a supplementary cross sectional image corresponding to the supplementary cross section Cp.

The process of constructing a cross sectional image as described above includes noise elimination (noise reduction), filtering, fast Fourier transform (FFT), etc. as with conventional Fourier domain OCT techniques. By applying fast Fourier transform, sampling data obtained by the data acquisition system 130 (i.e., interference signal, interferogram) is converted into an A-line profile. Such an A-line profile is a reflection intensity profile along the z direction. By performing imaging process on the A-line profile, that is, by assigning pixel values to the reflection intensity values in the A-line profile, an A-scan image is generated. Further, a two dimensional cross sectional image such as a B-scan image or a circle scan image is constructed by arranging a plurality of the A-scan images thus generated according to the scan pattern. In the case where an OCT apparatus of another type is employed, the cross sectional image constructing unit 221 executes a known process according to the OCT type employed.

<Phase Image Constructing Unit 222>

The phase image constructing unit 222 is configured to construct a phase image that represents a temporal change (or, temporal variation, chronological change, chronological variation, time course, or the like) in the phase differences in the cross section of interest, based on sampling data obtained by the data acquisition system 130 with the main scan. The sampling data used for constructing the phase image may be the same as the sampling data used for constructing the main cross sectional image by the cross sectional image constructing unit 221. Doing so makes it possible to perform registration between the main cross sectional image and the phase image. In other words, a natural correspondence may be defined between the pixels of the main cross sectional image and the pixels of the phase image.

An example will be described of a method of constructing such phase images. A phase image in the present example is obtained by calculating the phase difference between adjacent A-line complex signals (that is, signals corresponding to mutually adjacent scan points). In other words, the phase image in the present example is constructed based on the temporal change in the pixel values (brightness values) of the main cross sectional image. For an arbitrary pixel of the main cross sectional image, the phase image constructing unit 222 creates a graph of the temporal change in the brightness value of that pixel. The phase image constructing unit 222 determines the phase difference $\Delta\varphi$ between two time points t1 and t2 separated by a predetermined time interval $\Delta t$ in the graph created (t2=t1+$\Delta t$). Then, the phase difference $\Delta\varphi$ is defined as the phase difference $\Delta\varphi$ (t1) at the time point t1. More generally, the phase difference $\Delta\varphi$ may be defined as the phase difference at an arbitrary time point between the time points t1 and t2. By performing this process for each of a large number of time points set in advance, a temporal change in the phase difference for that pixel is obtained.

A phase image is an image representation of phase difference values of each pixel at each time point. This imaging process may be realized, for example, by representing the values of the phase difference with display colors or brightness. When applying such image representation, a display color indicating that a phase has increased in time series may be different from a display color indicating that a phase has decreased in time series. For example, red is assigned to phase increase, and blue is assigned to phase decrease. Further, the magnitude of the amount of change in a phase may be represented by the density of display colors. By adopting any of the representation methods or techniques as described above, the direction and quantity of blood flow may be clearly indicated using display colors. A phase image is constructed by executing the above processing for each pixel.

Note that the temporal change in phase difference may be obtained by sufficiently reducing the time interval $\Delta t$ described above to secure the correlation in phases. Here, oversampling may be performed in which the time interval $\Delta t$ is set to a value less than the time period corresponding to the resolution of a cross sectional image in the scanning of the measurement light LS.

<Data Processor 230>

The data processor 230 is configured to perform various kinds of data processing. For example, the data processor 230 applies various kinds of image processing and/or various kinds of analysis processing, to an image constructed by the image constructing unit 220. As a specific example, the data processor 230 performs various kinds of correction processing such as brightness correction or dispersion correction of an image. Further, the data processor 230 may be configured to perform various kinds of image processing and/or various kinds of analysis processing, on an image obtained by the fundus camera unit 2 (e.g., an fundus image, an anterior eye segment image), an image input from the outside, or other images.

The data processor 230 may is configured to construct three dimensional image data of the fundus Ef. Three dimensional image data means image data in which the positions of pixels are defined using a three dimensional coordinate system. Stack data and volume data are examples of such three dimensional image data.

Stack data is image data constructed by arranging a plurality of cross sectional images respectively obtained for a plurality of scan lines in an three dimensional fashion, based on the positional relationship of the scan lines. In other words, stack data is image data constructed by representing a plurality of cross sectional images, which are originally defined using mutually different two dimensional coordinate systems, using a common three dimensional coordinate system. In further other words, stack data is image data constructed by embedding such a plurality of cross sectional images in a common three dimensional space.

Volume data is image data whose picture elements are voxels that are arranged in a three dimensional manner. Volume data is also referred to as voxel data. Volume data is constructed by applying known interpolation, voxelization, or the like, to stack data.

The data processor 230 may construct an image to be displayed, by applying a rendering process to three dimensional image data. Examples of applicable rendering methods and techniques include volume rendering, surface rendering, maximum intensity projection (MIP), minimum intensity projection (MinIP), and multi planar reconstruction (MPR).

The data processor 230 includes, for example, a processor operable in accordance with a data processing program in order to execute the various kinds of data processing examples described above.

The data processor 230 includes the following elements for obtaining blood flow information as examples: the blood vessel region identifier 231, the blood flow information generator 232, and the region-of-interest (ROI) determining processor 260. The blood flow information generator 232 may include the gradient estimator 233, the blood flow velocity calculator 234, the blood vessel diameter calculator 235, and the blood flow amount calculator 236.

The region-of-interest determining processor 260 may include the blood-vessel-of-interest (BVOI) identifier 270. The blood-vessel-of-interest identifier 270 may include any one or both of the artery-of-interest (AOI) identifier 271 and the thick blood vessel (TBV) identifier 272. The region-of-interest determining processor 260 may include the position-of-interest (POI) identifier 280.

The blood vessel region identifier 231 includes, for example, a processor operable in accordance with a blood vessel region identifying program. The blood flow information generator 232 includes, for example, a processor operable in accordance with a blood flow information generating program. The gradient estimator 233 includes, for example, a processor operable in accordance with a gradient estimating program. The blood flow velocity calculator 234 includes, for example, a processor operable in accordance with a blood flow velocity calculating program. The blood vessel diameter calculator 235 includes, for example, a processor operable in accordance with a blood vessel diameter calculating program. The blood flow amount calculator 236 includes, for example, a processor operable in accordance with a blood flow amount calculating program. The region-of-interest determining processor 260 includes, for example, a processor operable in accordance with a region-of-interest determining program. The blood-vessel-of-interest identifier 270 includes, for example, a processor operable in accordance with a blood-vessel-of-interest identifying program. The artery-of-interest identifier 271 includes, for example, a processor operable in accordance with an artery-of-interest identifying program. The thick blood vessel identifier 272 includes, for example, a processor operable in accordance with a thick blood vessel identifying program. The position-of-interest identifier 280 includes, for example, a processor operable in accordance with a position-of-interest identifying program.

<Blood Vessel Region Identifier 231>

For each of the main cross sectional image, the supplementary cross sectional image, and the phase image, the blood vessel region identifier 231 identifies a blood vessel region in that image corresponding to the blood vessel of interest Db. Such segmentation may be performed by analyzing the pixel values of each image (e.g., thresholding).

Note that although the main cross sectional image and the supplementary cross sectional image have sufficient resolution to be subjected to analysis processing, the phase image may not have the resolution enough to identify the boundary of a blood vessel region in some cases. However, since blood flow information is generated based on the phase image, it is necessary to identify a blood vessel region included therein with high precision and high accuracy. To do so, for example, the following processes may be employed to more accurately identify a blood vessel region in the phase image.

As described above, the main cross sectional image and the phase image both are constructed from the same sampling data. Therefore, a natural correspondence between the pixels of the main cross sectional image and the pixels of the phase image may be defined and introduced. For example, the blood vessel region identifier 231 may be configured to perform the series of processes as follows in order to identify a blood vessel region in the phase image: a process of analyzing the main cross sectional image so as to identify a blood vessel region in the main cross sectional image; a process of identifying an image region in the phase image corresponding to the blood vessel region identified in the main cross sectional image, based on the pixel correspondence described above; and a process of adopting the image region identified in the phase image as a blood vessel region in the phase image. Such a series of processes makes it possible to identify a blood vessel region in the phase image with high precision and high accuracy.

<Blood Flow Information Generator 232>

The blood flow information generator 232 is configured to generate blood flow information on the blood vessel of interest Db. As described above, the blood flow information generator 232 includes the gradient estimator 233, the blood flow velocity calculator 234, the blood vessel diameter calculator 235, and the blood flow amount calculator 236.

<Gradient Estimator 233>

The gradient estimator 233 is configured to calculate an estimated value of the gradient of the blood vessel of interest Db based on data of the supplementary cross section (e.g., cross sectional data, supplementary cross sectional image) acquired by the supplementary scan described above. The estimated gradient value may be, for example, a measured value of the gradient of the blood vessel of interest at the cross section of interest, or an approximate value of such a measured value.

An example is described of the case in which the gradient value of a blood vessel of interest is actually measured (the first example of gradient estimation). In the case where the supplementary cross sections C1 and C2 shown in FIG. 5A are used, the gradient estimator 233 may calculate the gradient value of the blood vessel of interest Db at the cross section of interest C0, based on the positional relationship between the cross section of interest C0, the supplementary cross section C1, and the supplementary cross section C2, and based also on the result of the blood vessel regions identification executed by the blood vessel region identifier 231.

A method of calculating the gradient of the blood vessel of interest Db will be described with reference to FIG. 6A.

The reference characters G0, G1 and G2 indicate the main cross sectional image at the cross section of interest C0, the supplementary cross sectional image at the supplementary cross section C1, and the supplementary cross sectional image at the supplementary cross section C2, respectively. The reference characters V0, V1 and V2 indicate a blood vessel region in the main cross sectional image G0, a blood vessel region in the supplementary cross sectional image G1, and a blood vessel region in the supplementary cross sectional image G2, respectively. The z coordinate axis shown in FIG. 6A substantially coincides with the incident direction of the measurement light LS. Further, the distance between the main cross sectional image G0 (the cross section of interest C0) and the supplementary cross sectional image G1 (the supplementary cross section C1) is denoted by "d", and the distance between the main cross sectional image G0 (the cross section of interest C0) and the supplementary cross sectional image G2 (the supplementary cross section C2) is also denoted by the same "d". The interval between adjacent cross sectional images, that is, the interval between adjacent cross sections, is referred to as a distance between cross sections.

The gradient estimator 233 may calculate the gradient A of the blood vessel of interest Db at the cross section of interest C0 based on the positional relationship between the three blood vessel regions V0, V0 and V2. This positional relationship is determined, for example, by connecting the three blood vessel regions V0, V1 and V2. As a specific example, the gradient estimator 233 may identify feature positions respectively of the three blood vessel regions V0, V1 and V2, and then connect the feature positions identified. Examples of such a feature position include a center position, a center of gravity position, an uppermost location (i.e., the position having the smallest z coordinate value), a lowermost location (i.e., the position having the largest z coordinate value), and the like. Among these examples of feature positions, the identification of the uppermost location is considered to be the simplest processing. In addition, examples of methods of connecting the feature positions include a method of connecting with a line segment, a method of connecting with an approximate curve (e.g., spline curve, Bezier curve), and the like.

Further, the gradient estimator 233 calculates the gradient A based on the lines connecting the feature positions identified from the three blood vessel regions V0, V1 and V2. In the case of connecting with line segments, for example, the gradient A may be calculated based on the gradient of the first line segment and the gradient of the second line segment as follows. The first line segment connects the feature position of the cross section of interest C0 and the feature position of the supplementary cross section C1, and the second line segment connects the feature position of the cross section of interest C0 and the feature position of the supplementary cross section C2. An example of this calculation processing may be operated to calculate the average value of the gradients of the two line segments. On the other hand, an example of the case of connecting with an approximate curve may be operated to calculate the gradient of the approximate curve at the position where the approximate curve intersects the cross section of interest C0. Note that the distance between cross sections d may be used, for example, to embed the cross sectional images G0 to G2 in the xyz coordinate system in the process of determining a line segment or an approximate curve.

In the above examples, the blood vessel regions in three cross sections are taken into consideration; however, other examples may take two cross sections into consideration to calculate the gradient. As a specific example thereof, one of the gradient of the first line segment and the gradient of the second line segment mentioned above may be selected as a targeted gradient. Furthermore, the gradient A of the blood vessel of interest Db at the cross section of interest C0 may be calculated based on the two supplementary cross sectional images G1 and G2.

In the above examples, a single value of the gradient is obtained, but two or more values of the gradient may be obtained respectively for two or more positions (or regions) in the blood vessel region V0. If this is the case, the two or more gradient values obtained may be used separately. Alternatively, the two or more gradient values obtained may be subjected to statistical processing to derive a statistic (e.g., the mean value, the maximum value, the minimum value, the median, the mode), and the statistic may be used as the gradient A.

An example is described of the case in which an approximate value of the gradient of the blood vessel of interest is calculated (the second example of gradient estimation). In the event that the supplementary cross section Cp shown in FIG. 5B is applied, the gradient estimator 233 may analyze the supplementary cross sectional image corresponding to the supplementary cross section Cp to calculate an approximate value of the gradient of the blood vessel of interest Db at the cross section of interest C0.

A method of approximating the gradient of the blood vessel of interest Db will be described with reference to FIG. 6B. The reference character Gp indicates a supplementary cross sectional image of the supplementary cross section Cp. The reference character A indicates the gradient of the blood vessel of interest Db at the cross section of interest C0, as in the example shown in FIG. 6A.

In the present example, the gradient estimator 233 may identify an image region corresponding to a predetermined tissue of the fundus Ef by analyzing the supplementary cross sectional image Gp. For example, the gradient estimator 233 may identify an image region M corresponding to the inner limiting membrane (ILM) that is a surface tissue of the retina. The image region M is referred to as an inner limiting membrane region. For example, any known segmentation processing may be used to the image region identification.

It is known that the inner limiting membrane and fundus blood vessels are substantially parallel to each other. The gradient estimator 233 calculates the gradient $A_{app}$ of the inner limiting membrane region M at the cross section of interest C0. The gradient $A_{app}$ of the inner limiting membrane region M at the cross section of interest C0 may be used as an approximate value of the gradient A of the blood vessel of interest Db at the cross section of interest C0.

Figure 6A:
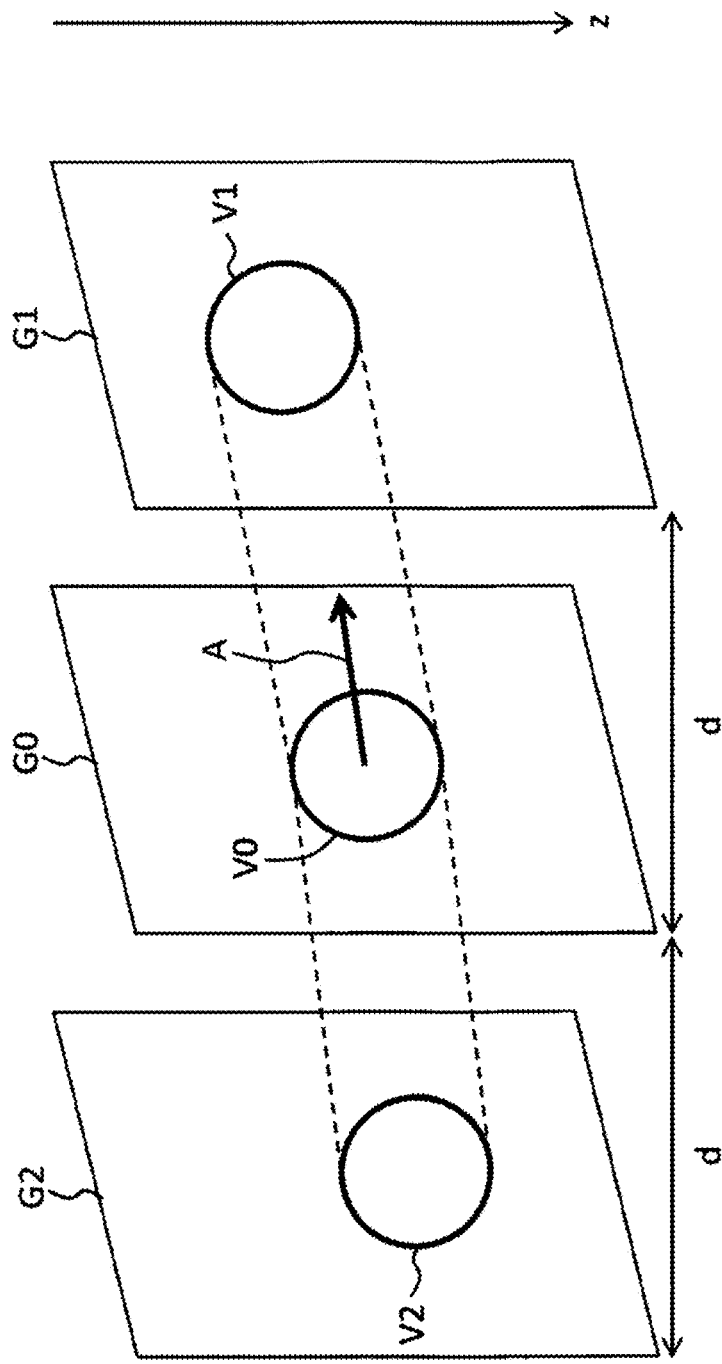
FIG. 6A is a schematic diagram for describing an example of the operation of the blood flow measurement apparatus according to the embodiment example.
Figure 6B:
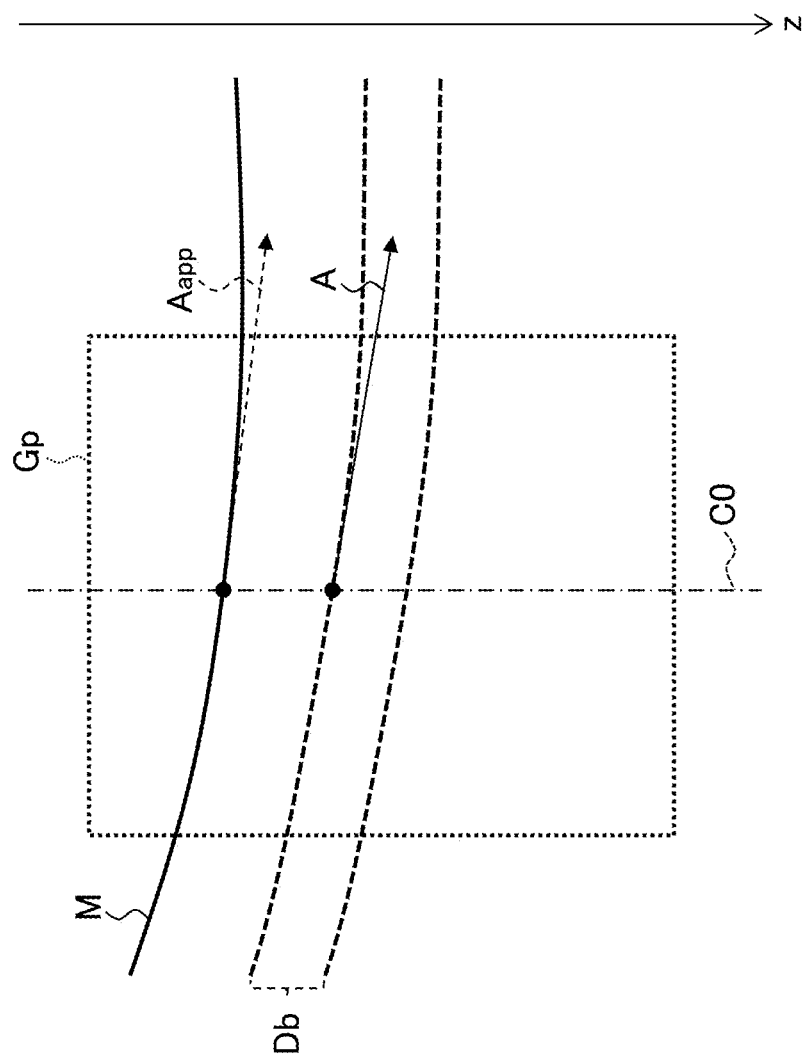
FIG. 6B is a schematic diagram for describing an example of the operation of the blood flow measurement apparatus according to the embodiment example.

Note that the gradient A shown in FIG. 6A and the gradient A shown in FIG. 6B are vectors representing the directions of the blood vessel of interest Db, and the definition of such vector values may be arbitrary. As an example, a value of the gradient A may be defined to be the angle formed by the gradient (vector) A and the z axis. Similarly, the gradient $A_{app}$ shown in FIG. 6B is a vector representing the orientation of the inner limiting membrane region M, and the definition of the value of the vector may be arbitrary. For example, the value of the gradient $A_{app}$ may be defined to be the angle formed by the gradient (vector) $A_{app}$ and the z axis. Note that the direction of the z axis is substantially the same as the incident direction of the measurement light LS.

In the third example of the gradient estimation of the blood vessel of interest, the gradient estimator 233 may analyze the supplementary cross sectional image Gp shown in FIG. 6B to identify an image region corresponding to the blood vessel of interest Db, and then calculate the gradient of the identified image region at the position corresponding to the cross section of interest C0. In such processing, the gradient estimator 233 may, for example, apply curve fitting to the boundary or the central axis of the image region corresponding to the blood vessel of interest Db, and then determine the gradient of the approximate curve, obtained by the curve fitting, at the position corresponding to the cross section of interest C0. A similar curve fitting technique may be applied to the image region corresponding to the predetermined tissue of the fundus Ef described above (e.g., the inner limiting membrane region M).

The processing executed by the gradient estimator 233 is not limited to the above processing examples, and may be any processing capable of deriving an estimated value of the gradient of the blood vessel of interest Db (e.g., a gradient value of the blood vessel of interest Db itself, a value approximating the gradient of the blood vessel of interest Db) based on cross sectional data acquired by applying OCT scanning to a cross section of the fundus Ef.

<Blood Flow Velocity Calculator 234>

Based on the temporal change in phase difference obtained as a phase image, the blood flow velocity calculator 234 calculates the blood flow velocity (or blood flow rate) at the cross section of interest C0 for blood flowing in the blood vessel of interest Db. A parameter obtained by this calculation may be blood flow velocity at a certain time point, or may be a temporal change in blood flow velocity. The temporal change in blood flow velocity is referred to as blood flow velocity variation information. When blood flow velocity at a certain time point is to be determined, the blood flow velocity at a predetermined time phase in an electrocardiogram (e.g., a time phase corresponding to the R wave) may be selectively acquired, for example. When blood flow velocity variation information is to be determined, a time period during which blood flow velocity is measured is the whole or an arbitrary part of the time period taken for OCT scanning of the cross section of interest C0.

When the blood flow velocity variation information is acquired, the blood flow velocity calculator 234 may further calculate a statistic of the blood flow velocity in the measurement period. Examples of the statistic include the mean value, the standard deviation, the variance, the median, the mode, the global maximum, the global minimum, the local maximum, and the local minimum. The blood flow velocity calculator 234 may create a histogram on the blood flow velocity values.

The blood flow velocity calculator 234 calculates the blood flow velocity using Doppler OCT technique. In the blood flow velocity calculation, the gradient A (or its approximate value $A_{app}$) of the blood vessel of interest Db at the cross section of interest C0 calculated by the gradient estimator 233 is taken into account. More specifically, the blood flow velocity calculator 234 may be configured to use the following relationship.

$$\Delta f = \frac{2nv\cos\theta}{\lambda}$$

Here: $\Delta f$ indicates the Doppler shift given to scattered light of the measurement light LS; n indicates the refractive index of medium; v indicates the flow velocity of the medium (blood flow velocity); θ indicates the angle between projection direction of the measurement light LS and the flow vector of the medium; and λ indicates the center wavelength of the measurement light LS.

In the present embodiment, n and λ are known, $\Delta f$ is derived from the temporal change of the phase difference, and θ is derived from the gradient A (or, from the approximate gradient value $A_{app}$). Typically, θ is equal to the gradient A (or, to the approximate gradient value $A_{app}$). Substituting these values into the above equation yields the blood flow velocity v.

<Blood Vessel Diameter Calculator 235>

The blood vessel diameter calculator 235 calculates the diameter of the blood vessel of interest Db at the cross section of interest C0. Examples of the blood vessel diameter calculation include the first calculation method on the basis of a fundus image (a front image of an eye fundus) and the second calculation method on the basis of a cross sectional image.

When applying the first calculation method, an area of the fundus Ef including the location of the cross section of interest C0 is photographed in advance. A fundus image thus obtained may be an observation image (e.g., a frame(s) thereof), or may be a photographed image. When the photographed image is a color image, any image obtained from the color image (e.g., a red-free image) may be used. The photographed image may be a fluorescence image obtained by fundus fluorescence angiography (e.g., fluorescein angiography), or may be a blood vessel emphasized image obtained by OCT angiography. An image created using OCT angiography is also referred to as an angiogram or a motion contrast image.

The blood vessel diameter calculator 235 sets a scale for fundus images based on various kinds of factors used to determine the relationship between the scale for images and the scale in the real space. Examples of such factors include the photographing angle of view (photographing magnification), the working distance, information on an ocular optical system. The scale for fundus images may represents a length in the real space. As a specific example, the scale for fundus images may be configured to associate interval between adjacent pixels (pixel pitch) with a scale (distance) in the real space (e.g., pixel pitch=10 μm). Note that it is possible to determine, in advance, the relationship between various values of the above factors and scales (values) in the real space, and then store a table or a graph that represents the relationship determined. In this case, the blood vessel diameter calculator 235 may select, from the table or the graph, a scale corresponding to the above factors and use the scale selected.

Based on the scale and the pixels included in the blood vessel region V0, the blood vessel diameter calculator 235 calculates the diameter of the blood vessel of interest Db at the cross section of interest C0, that is, the diameter of the blood vessel region V0. As a specific example, the blood vessel diameter calculator 235 may calculate the maximum or the mean value of a plurality of diameters of the blood vessel region V0 corresponding to different directions. In some other examples, the blood vessel diameter calculator 235 may determine an approximate circle or an approximate ellipse of the contour of the blood vessel region V0, and then calculate the diameter of the approximate circle or the approximate ellipse. Note that once the blood vessel diameter of the blood vessel region V0 is determined, the area of the blood vessel region V0 can (substantially) be calculated. That is, it is possible to substantially associate blood vessel diameters with blood vessel areas in one-to-one fashion. Therefore, an area of a blood vessel may be calculated in place of a diameter of the blood vessel.

The second calculation method will be described. In the second calculation method, typically, a cross sectional image at the cross section of interest C0 is used. The cross sectional image may be a main cross sectional image or any other image.

The scale of the cross sectional image is determined based on OCT measurement conditions. In the present embodiment, the cross section of interest C0 is scanned as shown in FIG. 5A or FIG. 5B. The length of the cross section of interest C0 is determined based on various kinds of factors that define the relationship between the scale of an image and the scale in the real space such as the working distance and information about ocular optical system. The blood vessel diameter calculator 235, for example, determines the pixel pitch based on the length of the cross section of interest C0, and calculates the diameter of the blood vessel of interest Db at the cross section of interest C0 in the same manner as in the first calculation method.

<Blood Flow Amount Calculator 236>

Based on the calculation result of the blood flow velocity and the calculation result of the blood vessel diameter, the blood flow amount calculator 236 calculates a flow amount (or, flow volume) of blood that flows in the blood vessel of interest Db. An example of the blood flow amount calculation will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following equation.

$$Q = \frac{\pi w^2}{8} Vm$$

The blood flow amount calculator 236 substitutes the blood vessel diameter w calculated by the blood vessel diameter calculator 235 and the maximum blood flow velocity Vm based on the blood flow velocity calculated by the blood flow velocity calculator 234 into the above equation, thereby determining the targeted blood flow amount Q.

<Region-of-Interest Determining Processor 260>

The region-of-interest determining processor 260 is configured to analyze a front image of the fundus Ef to determine a region of interest that intersects blood vessels of the fundus Ef. The region of interest is a cross section to which an OCT scan is to be applied. The region-of-interest determining processor 260 determines the region of interest by applying an arbitrary image analysis process to the front image of the fundus Ef.

The front image of the fundus Ef input to the region-of-interest determining processor 260 may be any kind of digital image that represents the morphology (or structure) of the fundus Ef. For example, the front image may be an image acquired by any ophthalmic modality such as a fundus camera, a scanning laser ophthalmoscope (SLO), an OCT apparatus, a slit lamp microscope, an ophthalmic surgical microscope, or another modality.

Further, the front image may be an image obtained by processing an image acquired by any ophthalmic modality. For example, the front image may be an image constructed by applying a rendering process to three dimensional image data acquired by a three dimensional OCT scan. Furthermore, the front image may be an image constructed by applying a rendering process to an arbitrary depth region (depth range, depth area) of three dimensional image data constructed by OCT angiography.

Some examples of the configuration and operation of the region-of-interest determining processor 260 will be described below.

The first example will be described. The region-of-interest determining processor 260 of the present example is configured to analyze a front image of the fundus Ef to identify a blood vessel of interest, and then determine a region of interest that intersects the blood vessel of interest identified. The region-of-interest determining processor 260 of the present example includes the blood-vessel-of-interest identifier 270.

The blood-vessel-of-interest identifier 270 is configured to identify a blood vessel of interest by analyzing a front image of the fundus Ef based on the blood vessel identification condition stored in the memory 212. The blood vessel identification condition and the blood vessel of interest identification processing executed on basis of the blood vessel identification condition have been described above. The region-of-interest determining processor 260 of the present example determines a region of interest in such a manner that the region of interest intersects the blood vessel of interest identified by the blood-vessel-of-interest identifier 270.

The second example will be described. The region-of-interest determining processor 260 of the present example is configured to analyze a front image of the fundus Ef to identify an artery of the fundus Ef (an artery of interest), and then determines a region of interest that intersects the artery of interest identified. The region-of-interest determining processor 260 of the present example includes the blood-vessel-of-interest identifier 270, and the blood-vessel-of-interest identifier 270 includes the artery-of-interest identifier 271.

The artery-of-interest identifier 271 is configured to selectively identify, as a blood vessel of interest identified by the blood-vessel-of-interest identifier 270, an artery (an artery of interest) rather than a vein. The blood vessel identification condition for identifying an artery of interest (the blood vessel type condition) and the processing executed on the basis of the blood vessel identification condition have been described above. The region-of-interest determining processor 260 of the present example determines a region of interest in such a manner that the region of interest intersects the artery of interest identified by the artery-of-interest identifier 271.

The third example will be described. The region-of-interest determining processor 260 of the present example is configured to analyze a front image of the fundus Ef to identify a blood vessel of the fundus Ef that has a thickness equal to or greater than a predetermined threshold value (a thick blood vessel), and then determines a region of interest that intersects the thick blood vessel identified. The region-of-interest determining processor 260 of the present example includes the blood-vessel-of-interest identifier 270, and the blood-vessel-of-interest identifier 270 includes the thick blood vessel identifier 272.

The thick blood vessel identifier 272 is configured to selectively identify, as a blood vessel of interest identified by the blood-vessel-of-interest identifier 270, a blood vessel with a thickness equal to or larger than a predetermined threshold value. The blood vessel identification condition for identifying a thick blood vessel (the blood vessel diameter condition) and the processing executed on the basis of the blood vessel identification condition have been described above. The region-of-interest determining processor 260 of the present example determines a region of interest in such a manner that the region of interest intersects the thick blood vessel identified by the thick blood vessel identifier 272.

The fourth example will be described. The region-of-interest determining processor 260 of the present example is configured to analyze a front image of the fundus Ef to identify an artery of the fundus Ef that has a thickness equal to or larger than a predetermined threshold value (a thick artery), and then determines a region of interest that intersects the thick artery identified. The region-of-interest determining processor 260 of the present example includes the blood-vessel-of-interest identifier 270, and the blood-vessel-of-interest identifier 270 includes both the artery-of-interest identifier 271 and the thick blood vessel identifier 272.

To begin with, a front image of the fundus Ef is input to the artery-of-interest identifier 271, for example. The artery-of-interest identifier 271 identifies one or more arteries in the manner described above. The result of the artery identification (and the front image) is input to the thick blood vessel identifier 272. The thick blood vessel identifier 272 identifies an artery that has a thickness equal to or larger than a predetermined threshold value, from among the one or more arteries identified by the artery-of-interest identifier 271 in the manner described above.

In some alternative examples, a front image of the fundus Ef is first input to the thick blood vessel identifier 272. The thick blood vessel identifier 272 identifies one or more thick blood vessels in the manner described above. The result of the thick blood vessel identification (and the front image) is input to the artery-of-interest identifier 271. The artery-of-interest identifier 271 identifies an artery from among the one or more thick blood vessels identified by the thick blood vessel identifier 272 in the manner described above.

The region-of-interest determining processor 260 of the present example determines a region of interest in such a manner that the region of interest intersects the thick artery identified by the combination of the artery-of-interest identifier 271 and the thick blood vessel identifier 272.

The fifth example will be described. In the present example, a front image of the fundus Ef includes an optic nerve head image. The blood-vessel-of-interest identifier 270 of the present example identifies, as a blood vessel of interest, a blood vessel having the largest diameter (a thickest blood vessel) in each of two or more regions located in mutually different directions with respect to the optic nerve head image, by analyzing the front image of the fundus Ef. The blood vessel identification condition for identifying the thickest blood vessel (the blood vessel position condition) and the processing executed on the basis of the blood vessel identification condition have been described above. For example, the blood-vessel-of-interest identifier 270 is configured to identify the four quadrants described above by analyzing the front image of the fundus Ef and then to identify the thickest blood vessel in each of the four quadrants.

The region-of-interest determining processor 260 of the present example determines a region of interest in such a manner that the region of interest intersects any one or more of the two or more thickest blood vessels respectively identified for the two or more regions by the blood-vessel-of-interest identifier 270. For example, the region-of-interest determining processor 260 selects any one or more thickest blood vessels from among the four thickest blood vessels respectively identified for the four quadrants, and then determines a region of interest in such a manner that the region of interest intersects the one or more thickest blood vessels selected. As an example, the region-of-interest determining processor 260 may be configured to select the thickest one from among the four thickest blood vessels and then determine a region of interest to intersect in such a manner that the region of interest intersects the selected blood vessel. As another example, the region-of-interest determining processor 260 may be configured to determine four regions of interest by determining a region of interest that intersects a corresponding thickest blood vessel for each of the four thickest blood vessels. As yet another example, the region-of-interest determining processor 260 may be configured to select one or more blood vessels, from among the four thickest blood vessels, whose thicknesses are equal to or larger than a predetermined threshold value, and determine a region of interest that intersects a corresponding blood vessel for each of the selected one or more blood vessels.

The sixth example will be described. In the present example, any of the second to fourth examples is combined with the fifth example.

In the case of combining the second example and the fifth example, the region-of-interest determining processor 260 is configured to: identify an artery having the largest diameter (a thickest artery) in each of two or more regions located in mutually different directions with respect to an optic nerve head image, by analyzing a front image of the fundus Ef; and determine a region of interest in such a manner that the region of interest intersects any one or more of the two or more thickest arteries respectively identified for the two or more regions.

In the case of combining the third example and the fifth example, the region-of-interest determining processor 260 is configured to: identify a blood vessel having a diameter equal to or larger than a predetermined threshold value and having the largest diameter (a thickest blood vessel) in each of two or more regions located in mutually different directions with respect to an optic nerve head image, by analyzing a front image of the fundus Ef; and determine a region of interest in such a manner that the region of interest intersects any one or more of the two or more thickest blood vessels respectively identified for the two or more regions.

In the case of combining the fourth example and the fifth example, the region-of-interest determining processor 260 is configured to: identify an artery having a diameter equal to or larger than a predetermined threshold value and having the largest diameter (a thickest artery) in each of two or more regions located in mutually different directions with respect to an optic nerve head image, by analyzing a front image of the fundus Ef; and determine a region of interest in such a manner that the region of interest intersects any one or more of the two or more thickest arteries respectively identified for the two or more regions.

The seventh example will be described. The region-of-interest determining processor 260 of the present example is configured to analyze a front image of the fundus Ef to identify a position of interest of a blood vessel and determine a region of interest in such a manner that the region of interest passes through the position of interest identified. The region-of-interest determining processor 260 of the present example includes the position-of-interest identifier 280.

The position-of-interest identifier 280 is configured to identifies a position of interest of a blood vessel by analyzing a front image of the fundus Ef based on the position identification condition stored in the memory 212. The position identification condition and the position of interest identification processing executed on the basis of the position identification condition have been described above. The region-of-interest determining processor 260 of the present example determines a region of interest in such a manner that the region of interest passes through the position of interest identified by the position-of-interest identifier 280.

The eighth example will be described. The region-of-interest determining processor 260 of the present example is configured to analyze a front image of the fundus Ef to identify a position located outside a blood vessel branching part as a position of interest, and determine a region of interest in such a manner that the region of interest passes through the position of interest identified. The region-of-interest determining processor 260 of the present example includes the position-of-interest identifier 280 configured to identify a position located outside a blood vessel branching part as a position of interest. The position identification condition for identifying a position located outside a blood vessel branching part as a position of interest (the branching condition) and the processing executed on the basis of the branching condition have been described above.

The ninth example will be described. The region-of-interest determining processor 260 of the present example is configured to analyze a front image of the fundus Ef to identify a position located outside a blood vessel tortuosity part as a position of interest, and determine a region of interest in such a manner that the region of interest passes through the position of interest identified. The region-of-interest determining processor 260 of the present example includes the position-of-interest identifier 280 configured to identify a position located outside a blood vessel tortuosity part as a position of interest. The position identification condition for identifying a position located outside a blood vessel tortuosity part as a position of interest (tortuosity condition) and the processing executed on the basis of the tortuosity condition have been described above.

The tenth example will be described. The region-of-interest determining processor 260 of the present example is configured to analyze a front image of the fundus Ef to identify a position located outside both a blood vessel branching part and a blood vessel tortuosity part as a position of interest, and determine a region of interest in such a manner that the region of interest passes through the position of interest identified. The region-of-interest determining processor 260 of the present example includes the position-of-interest identifier 280 configured to identify a position located outside both a blood vessel branching part and a blood vessel tortuosity part as a position of interest. The position identification condition for identifying a position located outside both a blood vessel branching part and a blood vessel tortuosity part as a position of interest includes both the branching condition and the tortuosity condition. Further, any one of the process of identifying a position located outside a blood vessel branching part based on the branching condition and the process of identifying a position located outside a blood vessel tortuosity part based on the tortuosity condition may be performed prior to another.

The eleventh example will be described. In the present example, a front image of the fundus Ef includes an optic nerve head image. The position-of-interest identifier 280 of the present example identifies a position located away from an optic nerve head image by a predetermined distance as the position of interest. The predetermined distance may be set based on the diameter of an optic nerve head of the fundus Ef (optic nerve head diameter). The predetermined distance of some examples may be a distance equal to an optic nerve head diameter. The position identification condition to be applied to the present example (the relative position condition) and the processing executed on the basis of the relative position condition have been described above.

The twelfth example will be described. In the present example, any of the eighth to tenth examples is combined with the eleventh example.

In the case of combining the eighth example and the eleventh example, the region-of-interest determining processor 260 is configured to: identify, as a position of interest, a position located away from an optic nerve head image by a predetermined distance and also located outside a blood vessel branching part; and determine a region of interest in such a manner that the region of interest passes through the position of interest identified.

In the case of combining the ninth example and the eleventh example, the region-of-interest determining processor 260 is configured to: identify, as a position of interest, a position located away from an optic nerve head image by a predetermined distance and also located outside a blood vessel tortuosity part; and determine a region of interest in such a manner that the region of interest passes through the position of interest identified.

In the case of combining the tenth example and the eleventh example, the region-of-interest determining processor 260 is configured to: identify, as a position of interest, a position located away from an optic nerve head image by a predetermined distance and also located outside both a blood vessel branching part and a blood vessel tortuosity part; and determine a region of interest in such a manner that the region of interest passes through the position of interest identified.

The thirteenth example will be described. The present example is a combination of any one or more of the first to sixth examples relating to the identification of a blood vessel of interest and any one or more of the seventh to twelfth examples relating to the identification of a position of interest. Combinations, configurations, and operations that are available (employable, usable, adoptable) as the thirteenth example could be understood by a person skilled in the art from the above descriptions and explanations on the first to twelfth examples. Therefore, the descriptions of each of such combinations will be omitted in order to avoid being redundant.

<User Interface 240>

The user interface (UI) 240 includes the display device 241 and the operation device 242. The display device 241 includes the display device 3 shown in FIG. 1 and/or another display device. The operation device 242 includes any types of operation devices. The user interface 240 may include, for example, a device having both a display function and an operation function, such as a touch panel.

<Data Input and Output Unit 290>

The data input and output unit 290 is configured to perform input of data into the blood flow measurement apparatus 1 and output of data from the blood flow measurement apparatus 1. For example, the data input and output unit 290 receives input of a front image of the fundus Ef.

The data input and output unit 290 has, for example, a function for communicating with external devices (not shown in the figures). The data input and output unit 290 with such a communication function includes a communication interface having a configuration depending on the form or aspect of connection with external devices. External devices may be, for example, one or more of any type of ophthalmic apparatus. Further, External devices may be one or more of any types of information processing devices such as a hospital information system (HIS) server, a digital imaging and communications in medicine (DICOM) server, a doctor's terminal, a mobile terminal, a personal terminal, a cloud server, and other devices.

The data input and output unit 290 may include a device that reads out information from a recording medium (i.e., a data reader device), and/or a device that writes or records information into a recording medium (i.e., a data writer device), for example.

<Operation of Blood Flow Measurement Apparatus>

Figure 7A:
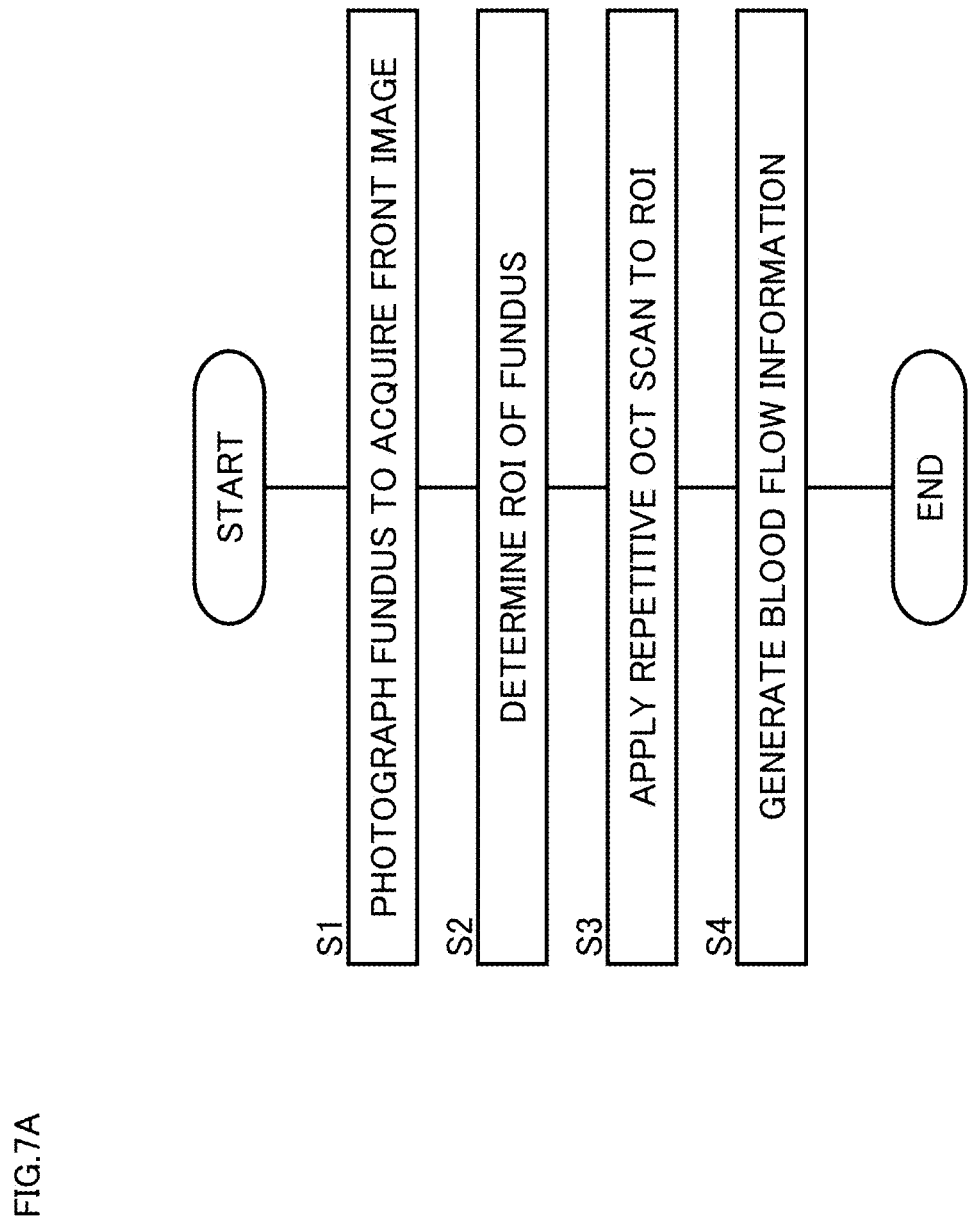
FIG. 7A is a flowchart showing an example of the operation of the blood flow measurement apparatus according to the embodiment example.
Figure 7B:
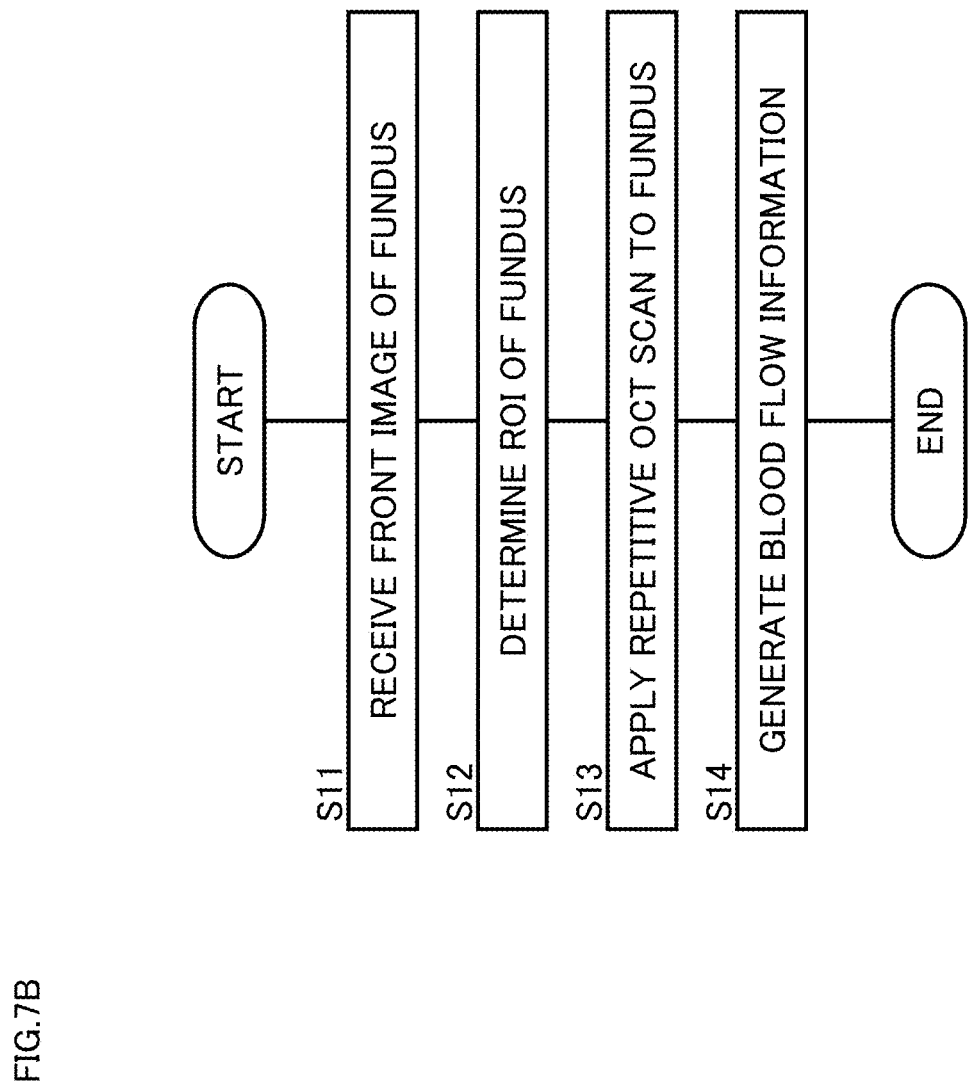
FIG. 7B is a flowchart showing an example of the operation of the blood flow measurement apparatus according to the embodiment example.

Some examples of the operation of the blood flow measurement apparatus 1 will be described below. FIG. 7A and FIG. 7B show two examples of the operation of the blood flow measurement apparatus 1. It is assumed that preparatory operations for fundus photography and OCT scanning, such as input of patient ID, alignment, focusing, and optical path length adjustment, have already been carried out prior to each of the examples.

First Operation Example

The first operation example will be described with reference to FIG. 7A.

(S1: Photograph Eye Fundus to Acquire Front Image)

First, the blood flow measurement apparatus 1 acquires a front image of the fundus Ef by photographing the fundus Ef using the fundus photography function (fundus camera function).

(S2: Determine Region of Interest of Eye Fundus)

The region-of-interest determining processor 260 analyzes the front image acquired in the step S1 to determine a region of interest that intersects one or more blood vessels of the fundus Ef.

The region of interest determined in the present example may have one or more of a plurality of features listed below: (1) the region of interest intersects one or more arteries of the fundus Ef; (2) the region of interest intersects one or more blood vessels that have diameters equal to or larger than a predetermined threshold value; (3) the region of interest passes through a position located outside blood vessel branching parts; (4) the region of interest passes through a position located outside blood vessel tortuosity parts; and (5) the region of interest passes through a position located away from an optic nerve head by a predetermined distance.

(S3: Apply Repetitive OCT Scan to Region of Interest)

The blood flow measurement apparatus 1 applies an OCT scan (a repetitive OCT scan) for blood flow measurement to the region of interest determined in the step S2.

Here, the mode of the repetitive OCT scan may be optional as long as an OCT scan is repeatedly applied (i.e., applied a plurality of times) to the same location. In the present operation example, the location to which the repetitive OCT scan is applied is the region of interest.

For example, the scan pattern of the repetitive OCT scan may be any pattern such as a line scan, a circle scan, or an arc pattern, and may be any pattern so that at least part of that pattern corresponds to the region of interest. Further, the patterns of a plurality of OCT scans performed in the repetitive OCT scan may or may not be the same. In the case where the scan patterns are not the same, the repetitive OCT scan may include both the first scan pattern (e.g., a circle scan) and the second scan pattern that is different from the first scan pattern (e.g., a circle scan).

In addition, the directions (orientations) of a plurality of OCT scans performed in the repetitive OCT scan may or may not be the same. In some examples of the case where the directions of the OCT scans are not the same, the repetitive OCT scan applied to a region of a linear shape whose both ends are referred to as the first end and the second end, may include both a scan oriented in the direction from the first end to the second end, and another scan oriented in the direction from the second end to the first end. In some alternative examples, the repetitive OCT scan applied to a region of a circular shape may include both a clockwise scan and a counterclockwise scan.

(S4: Generate Blood Flow Information)

The blood vessel region identifier 231 and the blood flow information generator 232 generate blood flow information based on the data collected by the repetitive OCT scan in the step S3.

The blood flow information represents one or more blood flow dynamics parameters (e.g., blood flow velocity, blood flow amount) for any of blood vessels passing through the region of interest determined in the step S2, that is, for any of blood vessels passing through the cross section to which the repetitive OCT scan of the step S3 is applied.

Second Operation Example

The second operation example will be described with reference to FIG. 7B.

(S11: Receive Front Image of Eye Fundus)

First, the blood flow measurement apparatus 1 receives a front image of the fundus Ef from, for example, an external device or a recording medium by using the data input and output unit 290.

(S12: Determine Region of Interest of Eye Fundus)

The region-of-interest determining processor 260 analyzes the front image acquired in the step S11 to determine a region of interest that intersects one or more blood vessels of the fundus Ef.

(S13: Apply Repetitive OCT Scan to Region of Interest)

The blood flow measurement apparatus 1 applies an OCT scan (a repetitive OCT scan) for blood flow measurement to the region of interest determined in the step S12.

(S14: Generate Blood Flow Information)

The blood vessel region identifier 231 and the blood flow information generator 232 generate blood flow information based on the data collected by the repetitive OCT scan in the step S13.

<Effects of Blood Flow Measurement Apparatus>

Some effects of the blood flow measurement apparatus according to some embodiment examples will be described.

The blood flow measurement apparatus of some embodiment examples includes a scanning optical system, a front image acquiring unit, a region-of-interest determining processor, a scan controller, and a blood flow information acquiring unit.

The scanning optical system is configured to apply OCT scanning to a fundus of a subject's eye. In the above embodiment example, the optical system that includes the OCT unit 100 and the measurement arm in the fundus camera unit 2, corresponds to an example of the scanning optical system.

The front image acquiring unit is configured to acquire a front image of the fundus of the subject's eye. The front image acquiring unit serves, for example, any of a fundus photography function and a data receiving function. In the above embodiment example, the fundus camera unit 2 that includes the illumination optical system 10 and the photography optical system 30, corresponds to an example of the front image acquiring unit having the fundus photography function. Further, the data input and output unit 290 corresponds to an example of the front image acquiring unit having the data receiving function. The front image may be an image acquired by any kinds of modalities.

The region-of-interest determining processor is configured to determine a region of interest that intersects a blood vessel, by analyzing the front image acquired by the front image acquiring unit based on one or more condition set in advance. The one or more predetermined conditions referred to in the analysis of the front image may include, for example, any one or both of a blood vessel identification condition and a position identification condition. Here, the blood vessel identification condition is a condition that is used for identifying an image of a blood vessel depicted in the front image, and the position identification condition is a condition that is used for identifying a specific position in the front image. Note that the predetermined conditions referred to in the analysis of the front image are not limited to these examples, and the kinds of conditions may be optional. In the above embodiment example, the region-of-interest determining processor 260 corresponds to an example of the region-of-interest determining processor. While the region-of-interest determining processor 260 given as an example includes several elements as shown in FIG. 4B, this is merely an example of the region-of-interest determining processor. Some other embodiment examples may employ a region-of-interest determining processor that does not include any one or more (some or all) of the elements shown in FIG. 4B.

The scan controller is configured to control the scanning optical system in such a manner that the scanning optical system applies a repetitive OCT scan to the region of interest determined by the region-of-interest determining processor. As mentioned above, the repetitive OCT scan is OCT scanning for blood flow measurement. The control executed by the scan controller may include, for example, any of control of a light source, control of an optical scanner, control of a detector, control of a data acquisition system, and the like. In the above embodiment example, the controller 210 (the main controller 211) corresponds to an example of the scan controller.

The blood flow information acquiring unit is configured to acquire blood flow information based on data collected by the repetitive OCT scan performed under the control of the scan controller. The blood flow information is, for example, information on predetermined one or more parameters indicating blood flow dynamics of an eye fundus. In the above embodiment example, the blood vessel region identifier 231 and the blood flow information generator 232 correspond to an example of the blood flow information acquiring unit.

According to such an embodiment example, it becomes possible to automatically determine a measurement position appropriate (suitable) for blood flow measurement (a region of interest) from a front image of the eye fundus and then perform OCT blood flow measurement. Therefore, it becomes unnecessary for the user to perform a troublesome task of determining the measurement position, and furthermore, the risk of performing blood flow measurement without having an appropriate measurement position determined, is reduced. This makes it possible to easily and quickly obtain clinically useful data that accurately reflects the actual blood flow dynamics.

In some embodiment examples of the blood flow measurement apparatus, the region-of-interest determining processor may include a blood-vessel-of-interest identifier. The blood-vessel-of-interest identifier is configured to identify a blood vessel of interest by analyzing the front image of the eye fundus acquired by the front image acquiring unit based on a blood vessel identification condition set in advance. The blood vessel of interest indicates one or more blood vessels selected, as a target or candidate target to which the blood flow measurement is to be applied, from among a plurality of blood vessels (blood vessel network, vascular network) depicted in the front image of the eye fundus. In the above embodiment example, the blood-vessel-of-interest identifier 270 corresponds to an example of the blood-vessel-of-interest identifier. The region-of-interest determining processor of the present example may be further configured to determine a region of interest that intersects the blood vessel of interest identified by the blood-vessel-of-interest identifier. The scan controller controls the scanning optical system to apply the repetitive OCT scan to the region of interest that intersects the blood vessel of interest determined in this way. In addition, the blood flow information acquiring unit acquires blood flow information on the blood vessel of interest based on the data collected by the repetitive OCT scan.

According to such an embodiment example, it becomes unnecessary for the user to perform a troublesome task of selecting a blood vessel appropriate (suitable) for blood flow measurement from among a large number of blood vessels running on the eye fundus. Furthermore, the risk of performing blood flow measurement without having an appropriate blood vessel designated is reduced. These advantages make it possible to easily and quickly obtain clinically useful data that accurately reflects the actual blood flow dynamics.

In some embodiment examples of the blood flow measurement apparatus, the blood-vessel-of-interest identifier included in the region-of-interest determining processor may include an artery-of-interest identifier configured to identify an artery of interest as a blood vessel of interest. The artery of interest indicates one or more arteries selected, as a target or candidate target to which the blood flow measurement is to be applied, from among the blood vessel network depicted in a front image of the eye fundus. In the above embodiment example, the artery-of-interest identifier 271 corresponds to an example of the artery-of-interest identifier. The region-of-interest determining processor of the present example may be further configured to determine a region of interest that intersects the artery of interest identified by the artery-of-interest identifier. The scan controller controls the scanning optical system to apply a repetitive OCT scan to the region of interest that intersects the artery of interest determined in this way. In addition, the blood flow information acquiring unit acquires blood flow information on the artery of interest based on the data collected by the repetitive OCT scan.

According to such an embodiment example, it becomes unnecessary for the user to perform a troublesome task of selecting an artery appropriate (suitable) for blood flow measurement from among a large number of blood vessels running on the fundus. Furthermore, the risk of performing blood flow measurement without having an appropriate artery designated is reduced. These advantages make it possible to easily and quickly obtain clinically useful data that accurately reflects the actual blood flow dynamics.

In some embodiment examples of the blood flow measurement apparatus, the blood-vessel-of-interest identifier included in the region-of-interest determining processor may include a thick blood vessel identifier configured to identify, as a blood vessel of interest, a thick blood vessel whose diameter is equal to or larger than a threshold value set in advance. The thick blood vessel indicates one or more relatively thick blood vessels selected, as a target or candidate target to which the blood flow measurement is to be applied, from among the blood vessel network depicted in a front image of the eye fundus. In the above embodiment example, the thick blood vessel identifier 272 corresponds to an example of the thick blood vessel identifier. The region-of-interest determining processor of the present example may be further configured to determine a region of interest that intersects the thick blood vessel identified by the thick blood vessel identifier. The scan controller controls the scanning optical system to apply a repetitive OCT scan to the region of interest that intersects the thick blood vessel determined in this way. In addition, the blood flow information acquiring unit acquires blood flow information on the thick blood vessel based on the data collected by the repetitive OCT scan.

According to such an embodiment example, it becomes unnecessary for the user to perform a troublesome task of selecting a thick blood vessel appropriate (suitable) for blood flow measurement from among a large number of blood vessels running on the eye fundus. Furthermore, the risk of performing blood flow measurement without having an appropriate thick blood vessel designated is reduced. These advantages make it possible to easily and quickly obtain clinically useful data that accurately reflects the actual blood flow dynamics.

In some embodiment examples of the blood flow measurement apparatus, the front image acquired by the front image acquiring unit may include an image of an optic nerve head (an optic nerve head image). In the case where a front image includes an optic nerve head image, that is, in the case where an optic nerve head is depicted in a front image, the blood-vessel-of-interest identifier included in the region-of-interest determining processor may identify, as a blood vessel of interest, a thickest blood vessel for each of two or more regions located in mutually different directions with respect to the optic nerve head image, wherein each of the two or more identified thickest blood vessels has the largest diameter in a corresponding region. The region-of-interest determining processor of the present example may further determine a region of interest that intersects any of the two or more thickest blood vessels identified respectively for the two or more regions by the blood-vessel-of-interest identifier. The scan controller controls the scanning optical system to apply a repetitive OCT scan to each of the one or more regions of interest determined in this way. In addition, the blood flow information acquiring unit acquires one or more pieces of blood flow information respectively on the one or more thickest blood vessels corresponding to the one or more regions of interest, based on the data collected by the repetitive OCT scan.

According to such an embodiment example, it becomes unnecessary for the user to perform a troublesome task of selecting the thickest blood vessel in each of the two or more regions of the eye fundus from among a large number of blood vessels running on the eye fundus. Furthermore, the risk of performing blood flow measurement without having an appropriate blood vessel designated is reduced. These advantages make it possible to easily and quickly obtain clinically useful data that accurately reflects the actual blood flow dynamics.

In some embodiment examples of the blood flow measurement apparatus, the region-of-interest determining processor may include a position-of-interest identifier. The position-of-interest identifier is configured to identify a position of interest of a blood vessel by analyzing a front image of the eye fundus acquired by the front image acquiring unit based on a position identification condition set in advance. The position of interest of a blood vessel indicates one or more positions (locations, sites) selected or determined, as a target or candidate target to which the blood flow measurement is to be applied, in the blood vessel network depicted in the front image of the eye fundus. In the above embodiment example, the position-of-interest identifier 280 corresponds to an example of the position-of-interest identifier. The region-of-interest determining processor of the present example may be further configured to determine a region of interest that passes through the position of interest identified by the position-of-interest identifier. The scan controller controls the scanning optical system to apply a repetitive OCT scan to the region of interest that passes through the position of interest determined in this way. In addition, the blood flow information acquiring unit acquires blood flow information at the position of interest based on the data collected by the repetitive OCT scan.

According to such an embodiment example, it becomes unnecessary for the user to perform a troublesome task of selecting an appropriate (suitable) position (location) in the eye fundus for the blood flow measurement. Furthermore, the risk of performing blood flow measurement without having an appropriate measurement position designated is reduced. These advantages make it possible to easily and quickly obtain clinically useful data that accurately reflects the actual blood flow dynamics.

In some embodiment examples of the blood flow measurement apparatus, the position-of-interest identifier included in the region-of-interest determining processor may be configured to identify a position outside a blood vessel branching part as a position of interest. The blood vessel branching part indicates a location where a blood vessel branches in the blood vessel network of the eye fundus. The region-of-interest determining processor of the present example may be further configured to determine a region of interest that passes through the position of interest outside the blood vessel branching part identified by the position-of-interest identifier. The scan controller controls the scanning optical system to apply a repetitive OCT scan to the region of interest that passes through the position of interest located outside the blood vessel branching part determined in this way. In addition, the blood flow information acquiring unit acquires blood flow information at the position of interest based on the data collected by the repetitive OCT scan.

According to such an embodiment example, it becomes unnecessary for the user to perform a troublesome task of determining a measurement position while avoiding blood vessel branching parts that are inappropriate for the blood flow measurement. Furthermore, the risk of performing blood flow measurement without having an appropriate measurement position designated is reduced. These advantages make it possible to easily and quickly obtain clinically useful data that accurately reflects the actual blood flow dynamics.

In some embodiment examples of the blood flow measurement apparatus, the position-of-interest identifier included in the region-of-interest determining processor may be configured to identify a position outside a blood vessel tortuosity part as a position of interest. The blood vessel tortuosity part indicates a location where the bending (or curve) of a blood vessel in the blood vessel network of the eye fundus is relatively large. The region-of-interest determining processor of the present example may be further configured to determine a region of interest that passes through the position of interest outside the blood vessel tortuosity part identified by the position-of-interest identifier. The scan controller controls the scanning optical system to apply a repetitive OCT scan to the region of interest that passes through the position of interest located outside the blood vessel tortuosity part determined in this way. In addition, the blood flow information acquiring unit acquires blood flow information at the position of interest based on the data collected by the repetitive OCT scan.

According to such an embodiment example, it becomes unnecessary for the user to perform a troublesome task of determining a measurement position while avoiding blood vessel tortuosity parts that are inappropriate for the blood flow measurement. Furthermore, the risk of performing blood flow measurement without having an appropriate measurement position designated is reduced. These advantages make it possible to easily and quickly obtain clinically useful data that accurately reflects the actual blood flow dynamics.

In some embodiment examples of the blood flow measurement apparatus, in the case where the front image acquired by the front image acquiring unit includes an optic nerve head image, the position-of-interest identifier included in the region-of-interest determining processor may identify one or more positions away from the optic nerve head image by a predetermined distance as a position of interest. The region-of-interest determining processor of the present example may further determine a region of interest that passes through the position of interest for each of the one or more positions of interest identified by the position-of-interest identifier. The scan controller controls the scanning optical system to apply a repetitive OCT scan to each of the one or more regions of interest determined in this way. In addition, the blood flow information acquiring unit acquires one or more pieces of blood flow information respectively on one or more blood vessels corresponding to the one or more regions of interest based on the data collected by the repetitive OCT scan.

According to such an embodiment example, it becomes unnecessary for the user to perform a troublesome task of determining, as a measurement position, a position appropriate for blood flow measurement, that is, a position away from the optic nerve head image by a predetermined distance. Furthermore, the risk of performing blood flow measurement without having an appropriate measurement position designated is reduced. These advantages make it possible to easily and quickly obtain clinically useful data that accurately reflects the actual blood flow dynamics.

While the above embodiment example is configured to directly apply a repetitive OCT scan to a region of interest determined by the region-of-interest determining processor, embodiment examples are not limited to this. For example, some embodiment examples may be configured to present a region of interest determined by the region-of-interest determining processor to the user. In some embodiment examples, a display controller (e.g., the controller 210) may display an image indicating a determined region of interest (a region of interest image) together with a fundus image. In some typical examples, the display controller may display a region of interest image on a fundus image.

A fundus image displayed together with a region of interest image may be any kind of image, and may typically be a front image. The front image may be a front image acquired by the front image acquiring unit, and may be, for example, a front image analyzed in the region of interest determining process (referred to as the first front image) or may be a front image different from the first front image (referred to as the second front image). In the case where the second front image is displayed, the positional relationship between the second front image and a region of interest can be determined by performing registration between the first front image and the second front image.

A fundus image displayed together with a region of interest image may be an image constructed from three dimensional image data. The positional relationship between a region of interest and the three dimensional image data may be obtained, for example, through registration between a projection image of the three dimensional image data and the first front image.

The user is capable of perceiving the position of the region of interest in the eye fundus by referring to the region of interest image (and the fundus image) displayed. Furthermore, the user may move the region of interest image using the operation device 242. With this operation, the user can set a region of interest at a desired position in the eye fundus. At this time, the ophthalmic apparatus may perform judgment whether or not a new region of interest set by the user is appropriate. The judgment processing may be performed, for example, by the region-of-interest determining processor based on any one or both of the blood vessel identification condition and the position identification condition described above. The final determination of a region of interest is performed by the user or the ophthalmic apparatus. The ophthalmic apparatus applies a repetitive OCT scan to the region of interest finally determined.

<Method of Controlling Blood Flow Measurement Apparatus, Program, and Recording Medium>

The embodiment example described above provides an example of a method of controlling a blood flow measurement apparatus configured to measure blood flow dynamics by applying OCT scanning to a fundus of a subject's eye. This control method includes a front image acquiring step, a region-of-interest determining step, a scanning step, and a blood flow information acquiring step.

In the front image acquiring step, the blood flow measurement apparatus is controlled to acquire a front image of the eye fundus. In the embodiment example above, the fundus camera unit 2 or the data input and output unit 290 executes the front image acquiring step under the control of the controller 210.

In the region-of-interest determining step, the blood flow measurement apparatus is controlled to determine a region of interest that intersects a blood vessel by analyzing the front image acquired in the front image acquiring step based on a condition set in advance. In the embodiment example above, the region-of-interest determining processor 260 executes the region-of-interest determining step under the control of the controller 210. In some aspect examples, the region-of-interest determining step may include a step of identifying a blood vessel of interest based on a blood vessel identification condition set in advance. This blood vessel of interest identifying step may include any one or more of a step of identifying an artery of interest, a step of identifying a thick blood vessel, and a step of identifying the thickest blood vessel. In some aspect examples, the region-of-interest determining step may include a step of identifying a position of interest based on a position identification condition set in advance. This position of interest identifying step may include any one or more of a step of identifying a position outside a blood vessel branching part as a position of interest, a step of identifying a position outside a blood vessel tortuosity part as a position of interest, and a step of identifying a position away from an optic nerve head by a predetermined distance as a position of interest.

In the scanning step, the blood flow measurement apparatus is controlled to apply a repetitive OCT scan to the region of interest determined in the region-of-interest determining step. In the above embodiment example, the scanning optical system configured to apply an OCT scan to the eye fundus executes the scanning step under the control of the controller 210.

In the blood flow information acquiring step, the blood flow measurement apparatus is controlled to acquire blood flow information based on data collected by the repetitive OCT scan performed in the scanning step. In the above embodiment example, the blood vessel region identifier 231 and the blood flow information generator 232 executes the blood flow information acquiring step under the control of the controller 210.

According to such control methods pertaining to the aspect examples, it becomes possible to automatically determine a measurement position appropriate (suitable) for blood flow measurement (a region of interest) from a front image of the eye fundus, and perform OCT blood flow measurement. Therefore, it becomes unnecessary for the user to perform a troublesome task of determining a measurement position, and the risk of performing blood flow measurement without having an appropriate measurement position designated is reduced. This makes it possible to easily and quickly obtain clinically useful data that accurately reflects the actual blood flow dynamics.

It is possible to configure a program causing a blood flow measurement apparatus that includes a computer to execute any of such control methods. It is also possible to create a computer-readable non-transitory recording medium that records such a program. The non-transitory recording medium may be in any form, and examples thereof include a magnetic disk, an optical disk, a magneto-optical disk, a semiconductor memory, and the like.

The embodiments disclosed herein merely provide some aspect examples of the present invention. A person who intends to implement the present invention may apply any modification (e.g., omission, substitution, replacement, addition, etc.) to the embodiments disclosed herein.

What is claimed is:

1. A blood flow measurement apparatus comprising:
   a scanning optical system including an optical coherence tomography (OCT) scanner and configured to apply optical coherence tomography scanning to a fundus of a subject's eye;
   a front image acquiring sensor or memory configured to acquire a front image of the fundus;
   processing circuitry configured to determine a region of interest that intersects a blood vessel by analyzing the front image based on a condition set in advance;
   the processing circuitry further configured to control the scanning optical system to apply a repetitive OCT scan to the region of interest; and
   the processing circuitry further configured to acquire blood flow information based on data collected by the repetitive OCT scan,
   wherein the processing circuitry is further configured to identify a blood vessel of interest by analyzing the front image based on a blood vessel identification condition set in advance, and the processing circuitry determines a region of interest that intersects the blood vessel of interest identified,
   the front image includes an optic nerve head image,
   the processing circuitry identifies, as the blood vessel of interest, a thickest blood vessel for each of two or more regions located in mutually different directions with respect to the optic nerve head image, the thickest blood vessel having a largest diameter in a corresponding region, and
   the processing circuitry determines the region of interest that intersects any of two or more thickest blood vessels identified for the two or more regions.

2. The blood flow measurement apparatus of claim 1, wherein the processing circuitry is further configured to identify an artery of interest as the blood vessel of interest.

3. The blood flow measurement apparatus of claim 1, wherein the processing circuitry is further configured to identify, as the blood vessel of interest, a thick blood vessel whose diameter is equal to or larger than a threshold value set in advance.

4. The blood flow measurement apparatus of claim 1, wherein the processing circuitry is further configured to identify a position of interest of a blood vessel by analyzing the front image based on a position identification condition set in advance, and the processing circuitry determines a region of interest that passes through the position of interest identified.

5. The blood flow measurement apparatus of claim 4, wherein the processing circuitry identifies a position outside a blood vessel branching part as the position of interest.

6. The blood flow measurement apparatus of claim 4, wherein the processing circuitry identifies a position outside a blood vessel tortuosity part as the position of interest.

7. The blood flow measurement apparatus of claim 4, wherein
   the front image includes an optic nerve head image, and
   the processing circuitry identifies a position away from the optic nerve head image by a predetermined distance as the position of interest.

8. A method of controlling a blood flow measurement apparatus that measures blood flow dynamics by applying optical coherence tomography (OCT) scanning to a fundus of a subject's eye, comprising:
   a front image acquiring step of acquiring a front image of the fundus;
   a region-of-interest determining step of determining a region of interest that intersects a blood vessel by analyzing the front image based on a condition set in advance;
   a scanning step of applying a repetitive OCT scan to the region of interest;
   a blood flow information acquiring step of acquiring blood flow information based on data collected by the repetitive OCT scan;
   identifying a blood vessel of interest by analyzing the front image based on a blood vessel identification condition set in advance;
   determining a region of interest that intersects the blood vessel of interest identified wherein the front image includes an optic nerve head image;
   identifying, as the blood vessel of interest, a thickest blood vessel for each of two or more regions located in mutually different directions with respect to the optic nerve head image, the thickest blood vessel having a largest diameter in a corresponding region; and
   determining the region of interest that intersects any of two or more thickest blood vessels identified for the two or more regions.

9. A computer-readable non-transitory recording medium that records a program causing a blood flow measurement apparatus that includes a computer to execute the method of claim 8.

* * * * *